US010744269B2

United States Patent
Veasey et al.

(10) Patent No.: US 10,744,269 B2
(45) Date of Patent: Aug. 18, 2020

(54) SUPPLEMENTAL DEVICE FOR ATTACHMENT TO AN INJECTION DEVICE

(71) Applicant: Sanofi-Aventis Deutschland GmbH, Frankfurt am Main (DE)

(72) Inventors: Robert Veasey, Warwickshire (GB); David Aubrey Plumptre, Worcestershire (GB); Paul Richard Draper, Worcestershire (GB); David Richard Mercer, Dorset (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/888,724

(22) PCT Filed: May 2, 2014

(86) PCT No.: PCT/EP2014/058970
§ 371 (c)(1),
(2) Date: Nov. 3, 2015

(87) PCT Pub. No.: WO2014/180745
PCT Pub. Date: Nov. 13, 2014

(65) Prior Publication Data
US 2016/0082192 A1 Mar. 24, 2016

(30) Foreign Application Priority Data
May 7, 2013 (EP) .................................. 13166724

(51) Int. Cl.
*A61M 5/315* (2006.01)
*G01D 5/26* (2006.01)
(Continued)

(52) U.S. Cl.
CPC ............. *A61M 5/3155* (2013.01); *G01D 5/26* (2013.01); *G01F 22/00* (2013.01);
(Continued)

(58) Field of Classification Search
CPC ........ A61M 5/3155; A61M 2205/3327; A61M 2205/505; A61M 5/315; A61M 5/31526;
(Continued)

(56) References Cited

U.S. PATENT DOCUMENTS

| 533,575 A | 2/1895 | Wilkens |
|---|---|---|
| 5,226,895 A | 7/1993 | Harris |

(Continued)

FOREIGN PATENT DOCUMENTS

| CN | 1099301 | 3/1995 |
|---|---|---|
| CN | 102427840 | 4/2012 |

(Continued)

OTHER PUBLICATIONS

International Preliminary Report on Patentability and Written Opinion in Application No. PCT/EP2014/058970, dated Nov. 10, 2015, 6 pages.

(Continued)

*Primary Examiner* — Kevin C Sirmons
*Assistant Examiner* — Tezita Z Watts
(74) *Attorney, Agent, or Firm* — Fish & Richardson P.C.

(57) ABSTRACT

A supplemental device for attachment to an injection device, the supplemental device comprising: an electromechanical switch arrangement having an open state and a closed state, the electromechanical switch arrangement comprising a protrusion configured to contact a surface of the injection device when a dose of zero units is dialled into the injection device, wherein the state of the switch arrangement is configured to change when a dose dialled into the attached injection device is decreased from one unit to zero units; and a processor arrangement configured to: detect one or more changes in the state of the electromechanical switch arrangement; and determine from the one or more state changes that a dose of zero units is dialled into the injection device.

13 Claims, 15 Drawing Sheets

(51) Int. Cl.
*G01F 22/00* (2006.01)
*G06F 19/00* (2018.01)

(52) U.S. Cl.
CPC . *G06F 19/3468* (2013.01); *A61M 2205/3327* (2013.01); *A61M 2205/505* (2013.01)

(58) Field of Classification Search
CPC ........ A61M 5/38; G01D 5/26; G06F 19/3468; G01F 22/00
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A * | 1/1996 | Gabriel | A61M 5/20 604/134 |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2009/0275916 A1 | 11/2009 | Harms et al. | |
| 2009/0318865 A1 * | 12/2009 | Moller | A61M 5/31583 604/135 |
| 2011/0313349 A1 * | 12/2011 | Krulevitch | A61M 5/24 604/65 |
| 2012/0065588 A1 * | 3/2012 | Cirillo | A61M 5/31525 604/111 |

FOREIGN PATENT DOCUMENTS

| | | |
|---|---|---|
| EP | 0615762 A1 | 9/1994 |
| EP | 0937471 A2 | 8/1999 |
| EP | 0937476 A2 | 8/1999 |
| WO | 9938554 A1 | 8/1999 |
| WO | 0110484 A1 | 2/2001 |
| WO | 2009024562 A1 | 2/2009 |
| WO | 2011117212 A1 | 9/2011 |
| WO | 2012046199 A1 | 4/2012 |

OTHER PUBLICATIONS

International Search Report in Application No. PCT/EP2014/058970, dated Jul. 31, 2014, 4 pages.

* cited by examiner

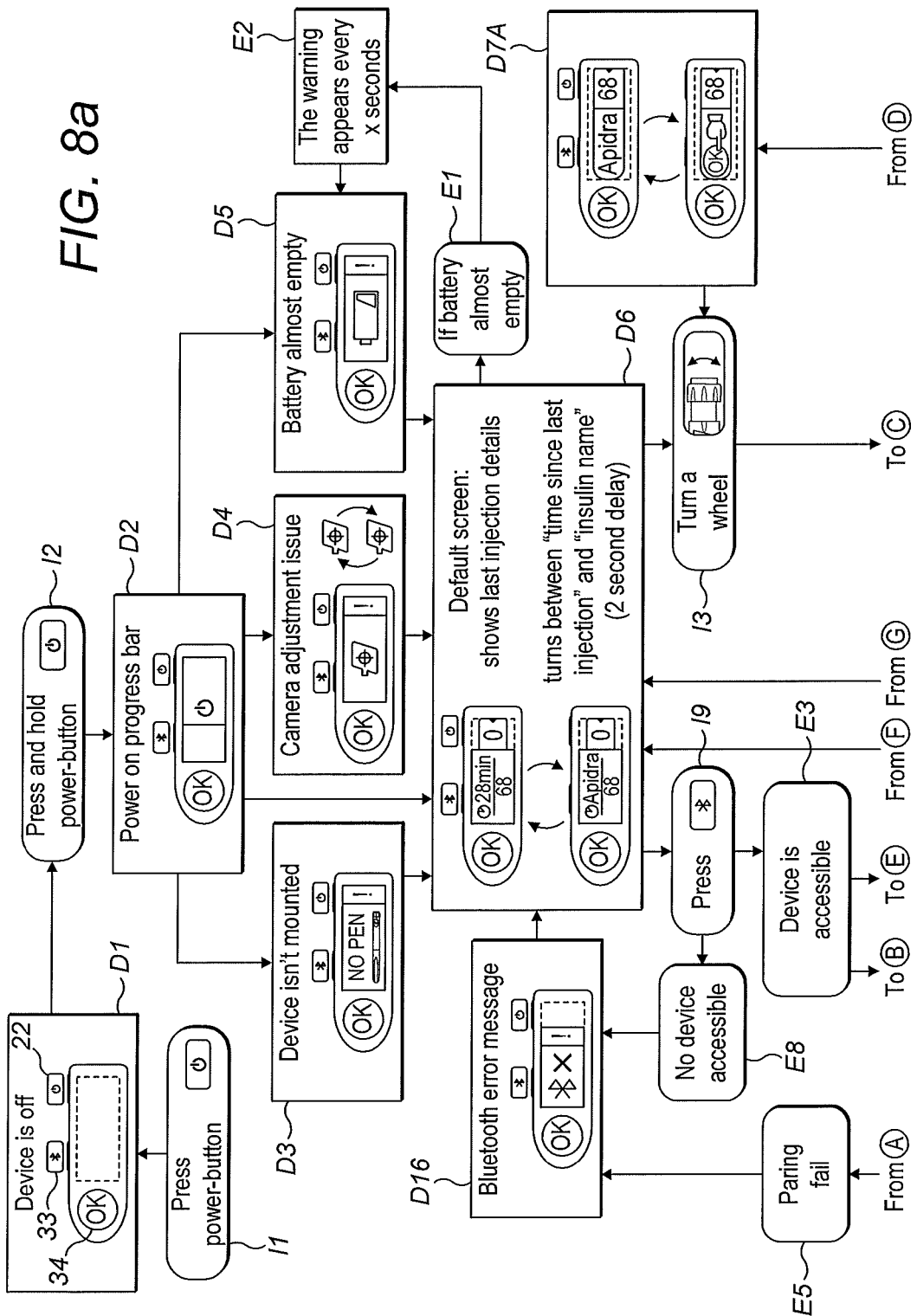

SUPPLEMENTAL DEVICE FOR ATTACHMENT TO AN INJECTION DEVICE

CROSS REFERENCE TO RELATED APPLICATIONS

The present application is a U.S. National Phase Application pursuant to 35 U.S.C. § 371 of International Application No. PCT/EP2014/058970 filed May 2, 2014, which claims priority to European Patent Application No. 13166724.8 filed May 7, 2013. The entire disclosure contents of these applications are herewith incorporated by reference into the present application.

FIELD OF INVENTION

The present invention relates to a supplemental device for attachment to an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

The control circuit of the medical device described in WO 2009/024562 can thus be used with a series of pre-filled disposable injection devices, but the requirement that the RFID unit with the value sensor is contained in the medicament container of the pre-filled disposable injection devices significantly increases the costs of the pre-filled disposable injection device.

It has been described, for instance in WO 2011/117212 to provide a supplementary device comprising a mating unit for releasably attaching the device to an injection device The device includes a camera and is configured to perform optical character recognition (OCR) on captured images visible through a dosage window of the injection pen, thereby to determine a dose of medicament that has been dialled into the injection device.

SUMMARY

A first aspect of the invention provides a supplemental device for attachment to an injection device, the supplemental device comprising:

an electromechanical switch arrangement having an open state and a closed state, the electromechanical switch arrangement comprising a protrusion configured to contact a surface of the injection device when a dose of zero units is dialled into the injection device, wherein the state of the switch arrangement is configured to change when a dose dialled into the attached injection device is decreased from one unit to zero units; and a processor arrangement configured to:

detect one or more changes in the state of the electromechanical switch arrangement; and determine from the one or more state changes that a dose of zero units is dialled into the injection device.

The protrusion may be further configured to contact the surface of the injection device when any number of dose units are dialled into the injection device. Alternatively, the protrusion may be further configured to contact the surface of the injection device only when a dose of zero units is dialled into the injection device.

The supplemental device may comprise:

a first electromechanical switch arrangement having an open state and a closed state, the first electromechanical switch arrangement comprising a first protrusion configured to contact a surface of the injection device when any number of dose units are dialled into the injection device; and a second electromechanical switch arrangement having an open state and a closed state, the second electromechanical switch arrangement comprising a second protrusion configured to contact a surface of the injection device only when a dose of zero units is dialled into the injection device.

The processor arrangement may be configured to determine whether each of the first and second electromechanical switch arrangements are open or closed. The processor arrangement may be configured to determine an amount of rotation of the surface of the injection device from signals received from the first electromechanical switch arrangement. The processor may be further configured, subsequent to determining from the one or more state changes that a dose of zero units is dialled into the injection device, to change a display output of the supplemental device from a dose delivery display to a dispense-end display. The processor may be further configured, subsequent to determining from the one or more state changes that a dose of zero units is dialled into the injection device, to place the supplemental device into a power saving mode.

The supplemental device may further comprise a dose dialled detector operable to detect a dose of medicament dialled into the attached injection device. The dose dialled detector may comprise an image capture device and an optical character recognition system.

A second aspect of the invention provides a system comprising a supplemental device according to the first aspect of the invention and an injection device.

The injection device of the second aspect of the invention may comprise:

a housing;

a corrugated dialling sleeve rotatably supported within the housing, the corrugated dialling sleeve having a plurality of axially aligned corrugations; and a rotatable dosage knob coupled to the corrugated dialling sleeve at a first end of the corrugated dialling sleeve, wherein the protrusion of the electromechanical switch arrangement is configured to engage the corrugated dialling sleeve.

Each of a plurality of troughs forming the corrugations may terminate at the first end of the corrugated dialling sleeve with an incline.

The rotatable dosage knob may have a larger diameter than the corrugated dialling sleeve and may define a flange at the first end of the corrugated dialling sleeve.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1A:
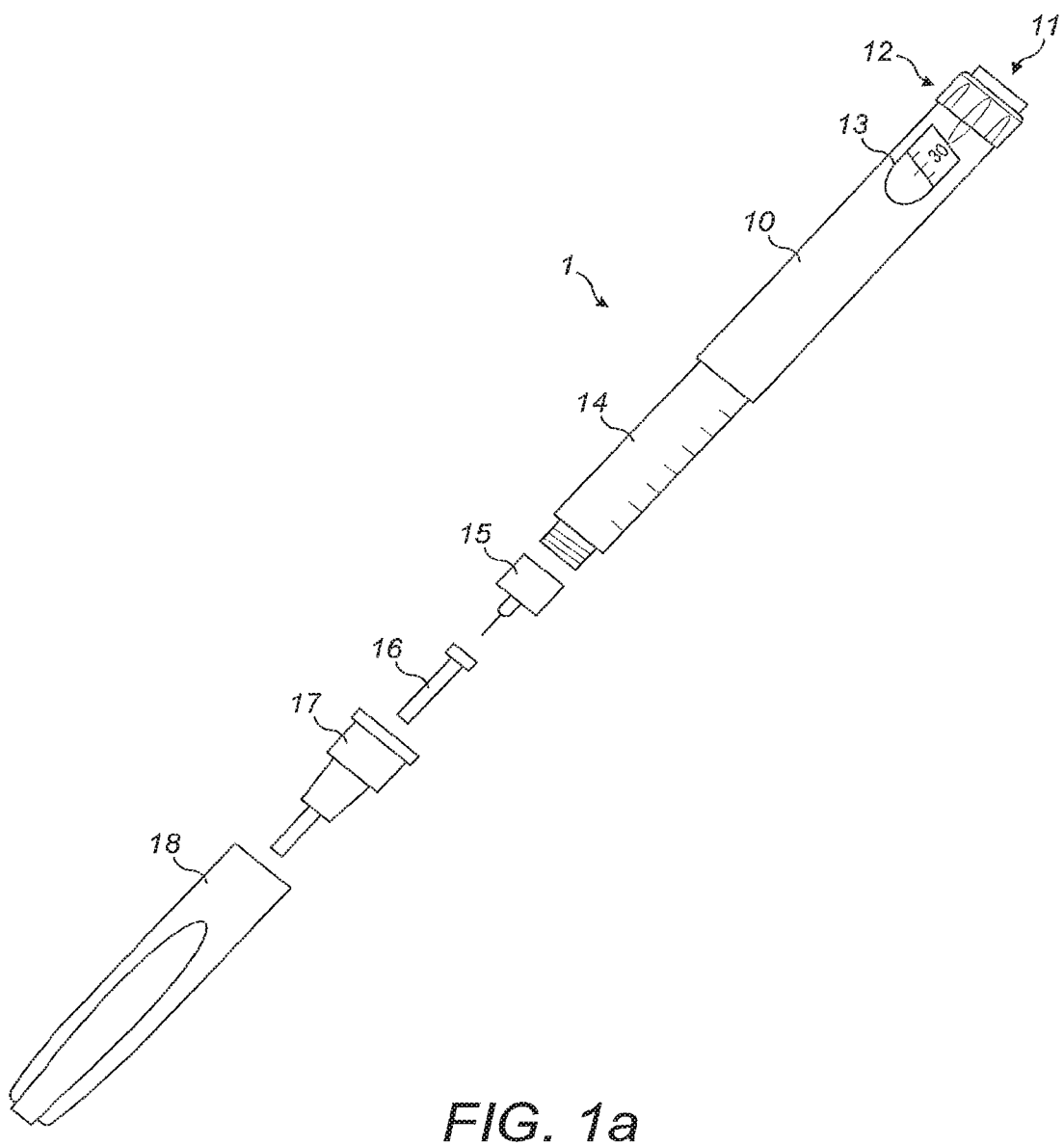
FIG. 1a: an exploded view of an injection device.
Figure 1B:
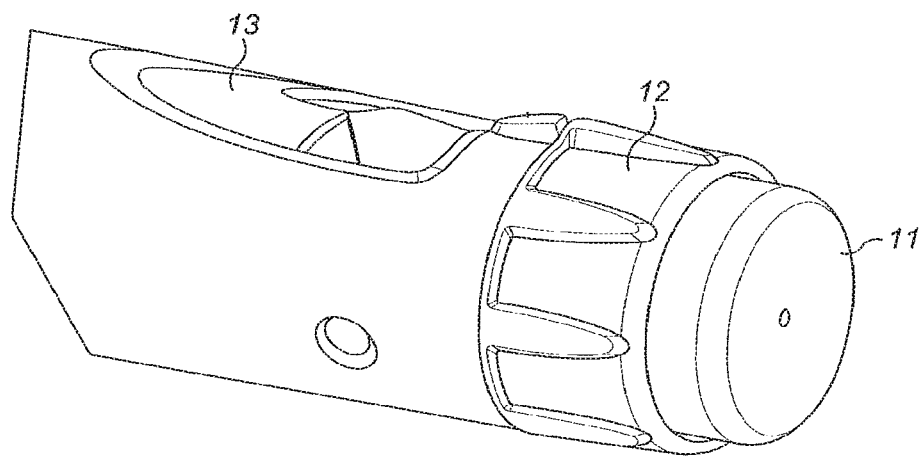
FIG. 1b shows a perspective view of some detail of the injection device of FIG. 1.

FIG. 1 is an exploded view of an injection device 1, which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently, for instance by means of an electronic display.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 2A:
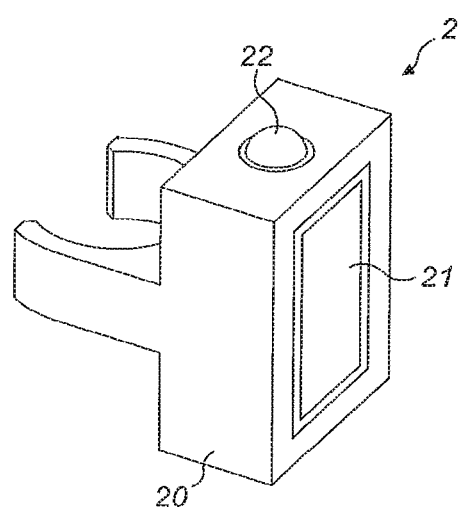
FIG. 2a: a schematic illustration of a supplementary device to be releasably attached to the injection device of FIG. 1 according to an aspect of the present invention.

FIG. 2a is a schematic illustration of an embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. Information is displayed via display unit 21 of supplementary device 2. The dosage window 13 of injection device 1 is obstructed by supplementary device 2 when attached to injection device 1.

Supplementary device 2 further comprises three user input transducers, illustrated schematically as a button 22. The button 22 allows a user to turn on/off supplementary device 2, to trigger actions (for instance to cause establishment of a connection to or a pairing with another device, and/or to trigger transmission of information from supplementary device 2 to another device), or to confirm something.

Figure 2B:
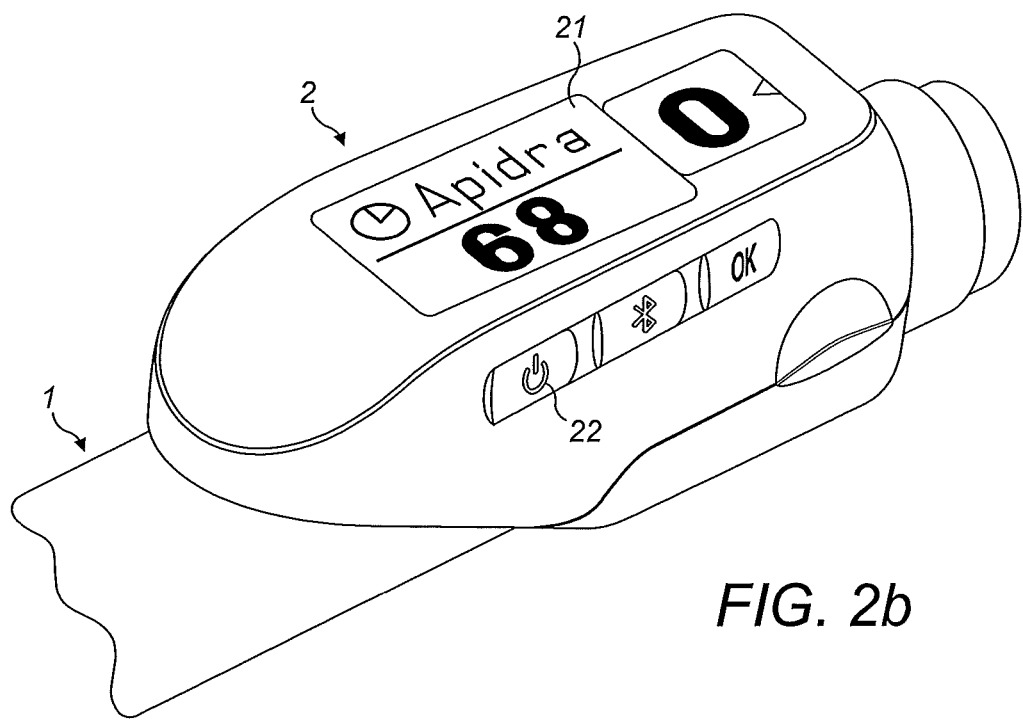
FIG. 2b: a perspective view of a supplementary device to be releasably attached to the injection device of FIG. 1 according to various aspects of the present invention.

FIG. 2b is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These iwout-buttons 22 allows a user to turn on/off supplementary device 2, to trigger actions (for instance to cause establishment of a connection to or a pairing with another device, and/or to trigger transmission of information from supplementary device 2 to another device), or to confirm something.

Figure 2C:
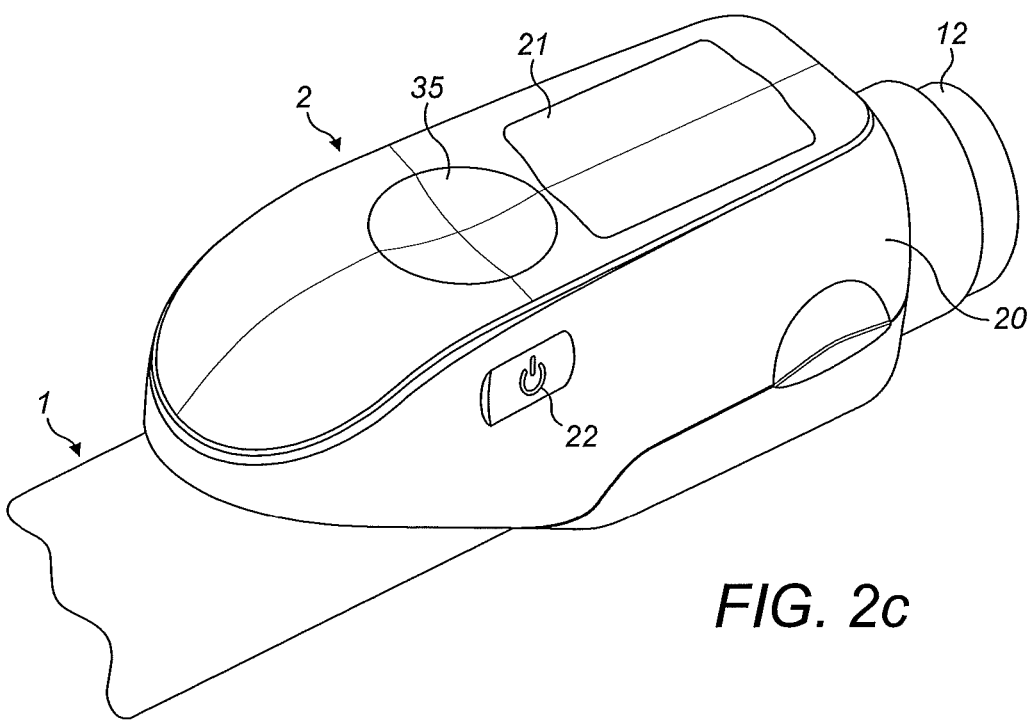
FIG. 2c: a perspective view of a supplementary device to be releasably attached to the injection device of FIG. 1 according to other aspects of the present invention.

FIG. 2c is a schematic illustration of a third embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a button 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3A:
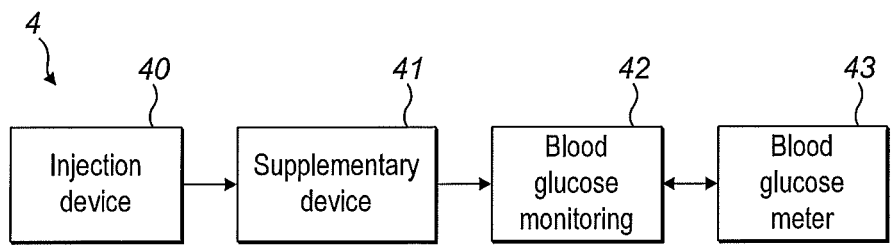
FIGS. 3a and 3b: possible distributions of functions among devices when using a supplementary device (such as the supplementary devices of FIGS. 2a, 2b and 2c) together with an injection device.
Figure 3B:
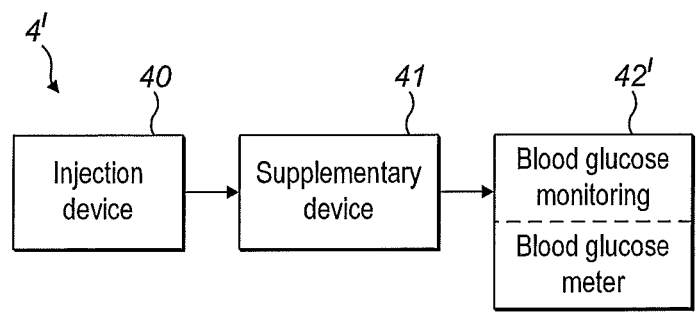

FIGS. 3A and 3b show possible distributions of functions among devices when using a supplementary device (such as the supplementary devices of FIGS. 2a and 2b) together with an injection device.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification. Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

Figure 4:
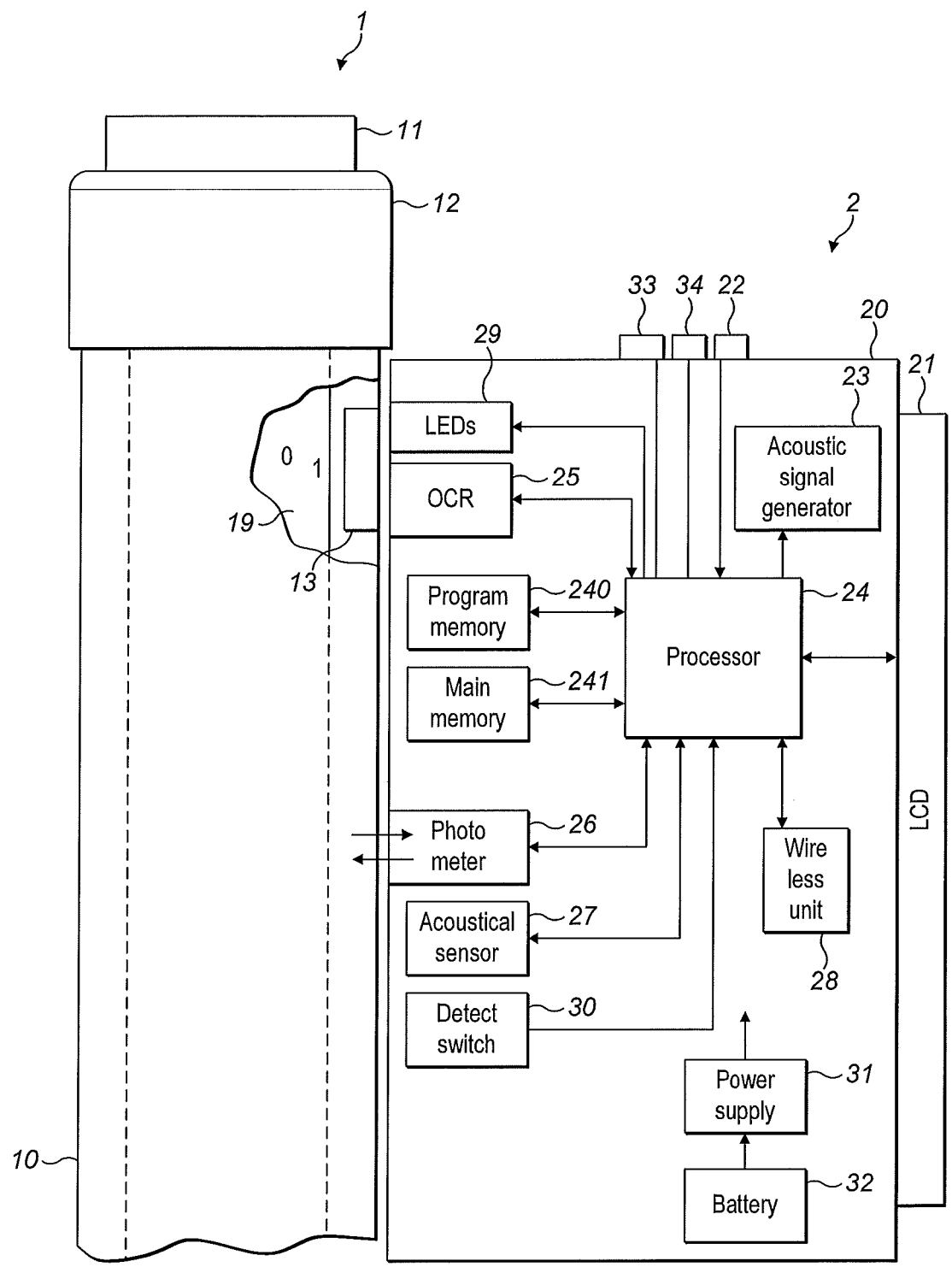
FIG. 4: a schematic view of the supplementary device of FIG. 2a in a state where it is attached to the injection device of FIG. 1.

FIG. 4 shows a schematic view of the supplementary device 2 of FIG. 2a in a state where it is attached to injection device 1 of FIG. 1.

With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2.

In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by means of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus® with purple colour and SoloStar Apidra® with blue colour). Alternatively, a camera unit may be used instead of photometer 26, and an image of the housing, sleeve or insulin container may then be provided to processor 24 to determine the colour of the housing, sleeve or insulin container by means of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by means of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

The processor 24 constitutes a processor arrangement. The OCR reader 25 constitutes a dose dialled detector operable to detect a dose of medicament dialled. The PCR reader 25 also constitutes a dose delivery determiner for determining that a dose of medicament has been delivered. The OCR reader 25 and the processor 24 together constitute a quantity determiner for determining a quantity of medicament that has been delivered. The processor 24 provides a function of a clock configured to determine a current time.

Figure 5A:
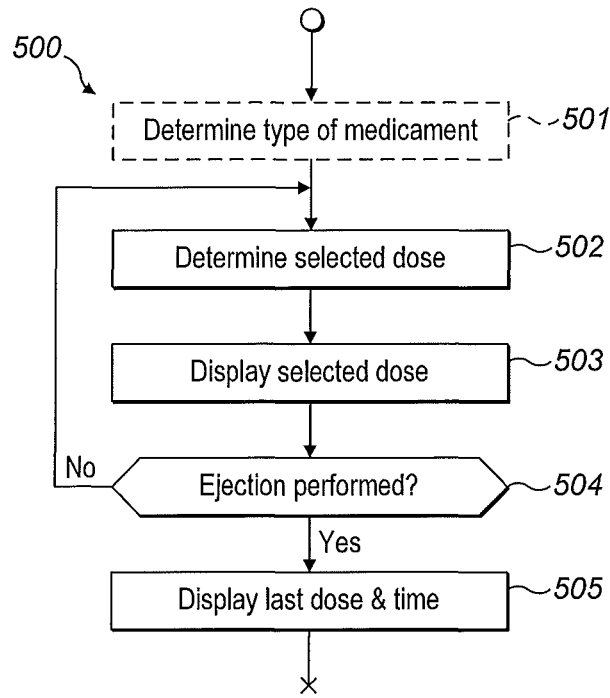
FIG. 5a: a flowchart of a method used in various aspects.
Figure 5B:
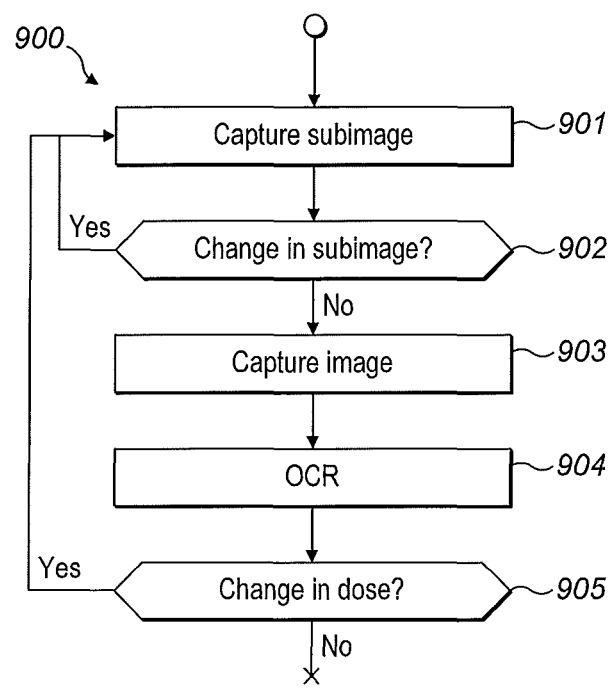
FIG. 5b: a flowchart of a further method used in various aspects.
Figure 5C:
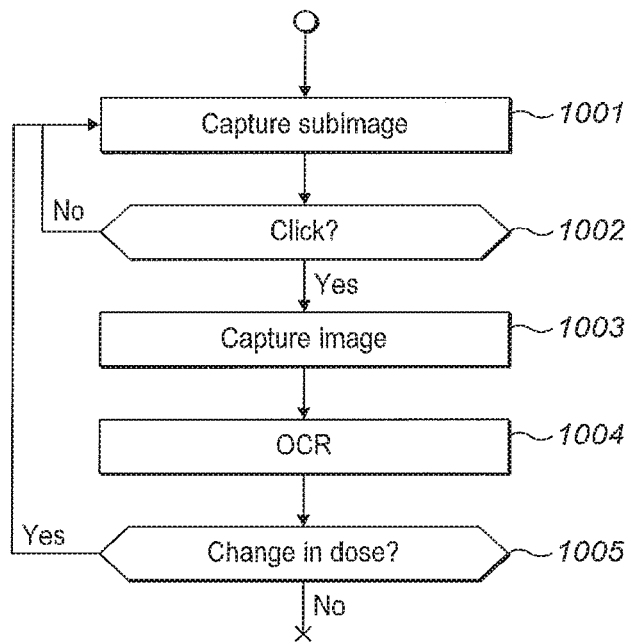
FIG. 5c: a flowchart of a still further method used in various aspects.

FIGS. 5a-5c are flowcharts of embodiments of methods according to the present invention. These methods may for instance be performed by processor 24 of supplementary device 2 (see FIGS. 2b and 4), but also by a processor of supplementary device 3 of FIG. 2b, and may for instance be stored in program memory 240 of supplementary device 2, which may for instance take the shape of tangible storage medium 60 of FIG. 6.

FIG. 5a shows method steps that are performed in scenarios as shown in FIGS. 3a and 3b, where information read by supplementary device 41 from injection device 40 is provided to blood glucose monitoring system 42 or 42' without receiving information back from blood glucose monitoring system 42 or 42'.

The flowchart 500 starts for instance when the supplementary device is turned on or is otherwise activated. In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage window of injection device as described above. This information is then displayed to a user of the injection device in a step 503.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is stored in the main memory 241, from where it may later be transmitted to another device, for instance a blood glucose monitoring system. If a differentiation has been made concerning the nature of the ejection, for instance if the ejection was performed as a prime shot or as an actual injection, this information may also be stored in the main memory 241, and possibly later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, the flowchart 500 terminates.

FIG. 5b shows in more detail exemplary method steps that are performed when the selected dose is determined based on the use of optical sensors only. For instance, these steps may be performed in step 502 of FIG. 5a.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by means of numbers and/or a scale printed on the sleeve 19 of injection device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of injection device 1 which is visible through dosage window 13. After capturing an image, it is, for instance, further processed as follows:

Division by a previously captured background image;
Binning of the image(s) to reduce the number of pixels for further evaluations;
Normalization of the image(s) to reduce intensity variations in the illumination;
Sheering of the image(s); and/or
Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplementary device 2. The captured image is for instance an image of the dosage window 13 of injection device 1, in which a currently selected dose is displayed (e.g. by means of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

FIG. 5c shows in more detail method steps that are performed when the selected dose is determined based on the use of acoustical and optical sensors. For instance, these steps may be performed in step 502 of FIG. 5a.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialled by turning dosage knob 12 of injection device 1 and/or when a dose is ejected/injected by pressing injection button 11, and/or when a prime shot is performed. If the captured sound is not a click sound, step 1001 is repeated. Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5c when it comes to power consumption of the supplementary device, because permanently capturing images or sub-images as shown in FIG. 5b typically is more power consuming than listening to an acoustical sensor such as a microphone.

Figure 6:
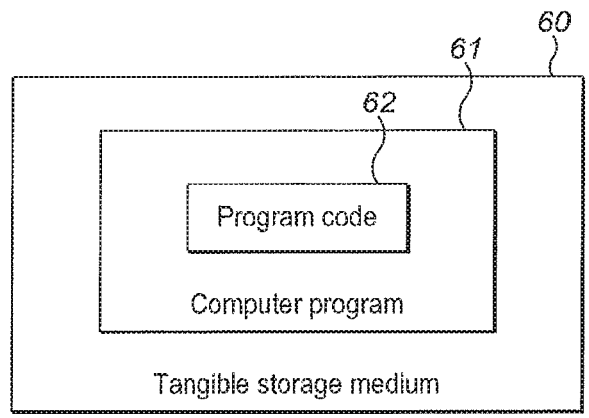
FIG. 6: a schematic illustration of a tangible storage medium 60 according to an aspect of the present invention.

FIG. 6 is a schematic illustration of a tangible storage medium 60 (a computer program product) that comprises a computer program 61 with program code 62 according to aspects of the present invention. This program code may for instance be executed by processors contained in the supplementary device, for instance processor 24 of supplementary device 2 of FIGS. 2a and 4. For instance, storage medium 60 may represent program memory 240 of supplementary device 2 of FIG. 4. Storage medium 60 may be a fixed memory, or a removable memory, such as for instance a memory stick or card.

Figure 7:
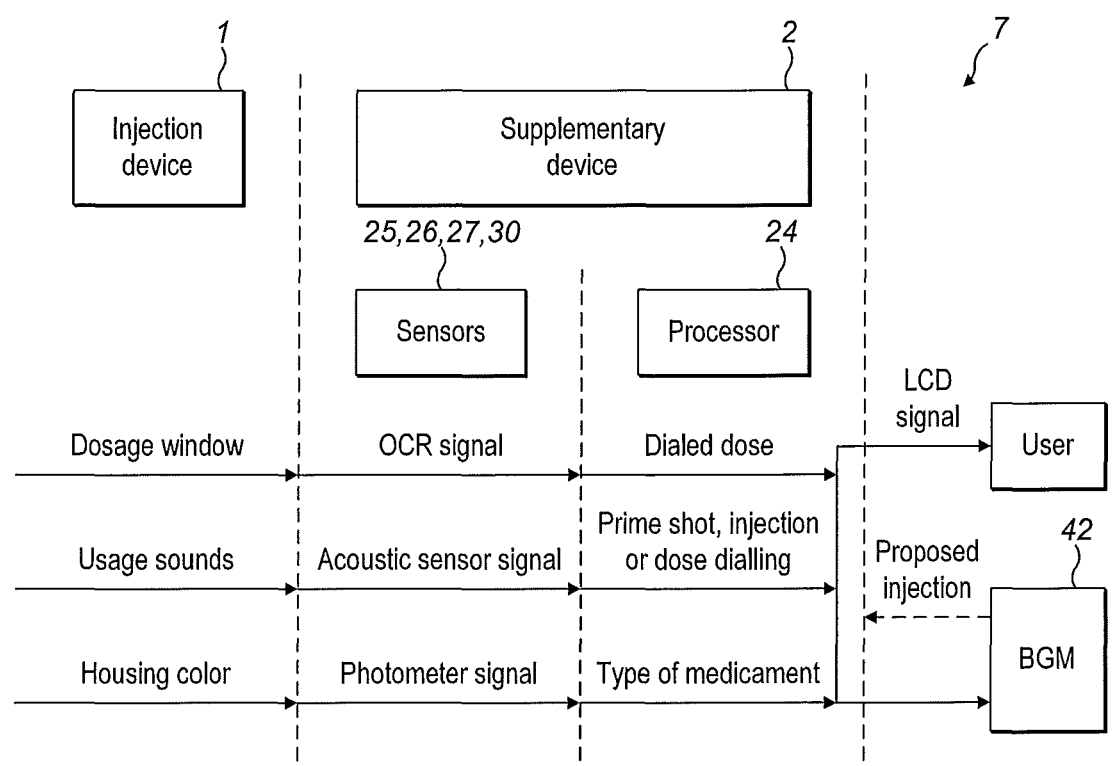
FIG. 7: an information sequence chart that illustrates an information flow between various devices according to aspects of the invention.

Finally, FIG. 7 is an information sequence chart 7 that illustrates the flow of information between various devices (e.g. the injection device 1 and the supplementary device 2 of FIG. 4 in a scenario as depicted in FIG. 3a or 3b) according to an embodiment of the present invention. A condition and/or use of injection device 1 affects an appearance of its dosage window, sounds generated by injection device 1 and a colour of the housing. This information is transformed by sensors 25, 26, 27, 30 of supplementary device 2 into an OCR signal, an acoustic sensor signal and a photometer signal, respectively, which are in turn transformed into information on the dialled dose, on an injection/dialling operation and on the type of insulin by a processor 24 of supplementary device 2, respectively. This information is then provided by supplementary device 2 to a blood glucose monitoring system 42. Some or all of this information is displayed to a user via the display 21.

As described in detail above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen. The supplementary device reads out the injected dose. It may also transfer it to a blood glucose monitoring system with insulin titration capabilities. For patients taking multiple insulins, the supplementary device recognizes the device structure to the insulin type and may also transmit this piece of information to the blood glucose monitoring system.

In example embodiments, the information shown on a display, for example LCD display 21 of FIGS. 2a and 4, may also converted to a sound signal played to a user through a speaker, for example by a text-to-speech functionality implemented by processor 24 using the acoustical signal generator 23. Thus, a user with impaired vision may have improved access to the information of supplementary device 2, such as a dialled dose, a recommended dose, a recommended time for administration and/or the like.

When using embodiments of the present invention, the user inter alia has the following advantages:

The user can use the most convenient disposable insulin injector.

The supplementary device is attachable and detachable (reusable).

Injected dose information may be transferred to the blood glucose monitoring system automatically (no more transfer mistakes). Improved dose guidance may result from this as the blood glucose monitoring system calculates the dose to be taken.

Keeping of a manual data logbook may not be needed any more.

Furthermore, when deploying the supplementary device proposed by the present invention, patients may also be reminded of injecting their next dose by receiving an alarm signal, for instance, after an appropriate time after a first dose of a medicament (for instance insulin or heparin) has been injected.

Injected dose information may be transferred to any computerized system, for instance as input for any dose calculation or any other applicable therapeutic guidance calculation, or for the creation of an alarm signal, for instance to remind the user of taking the next dose.

Figure 8B:
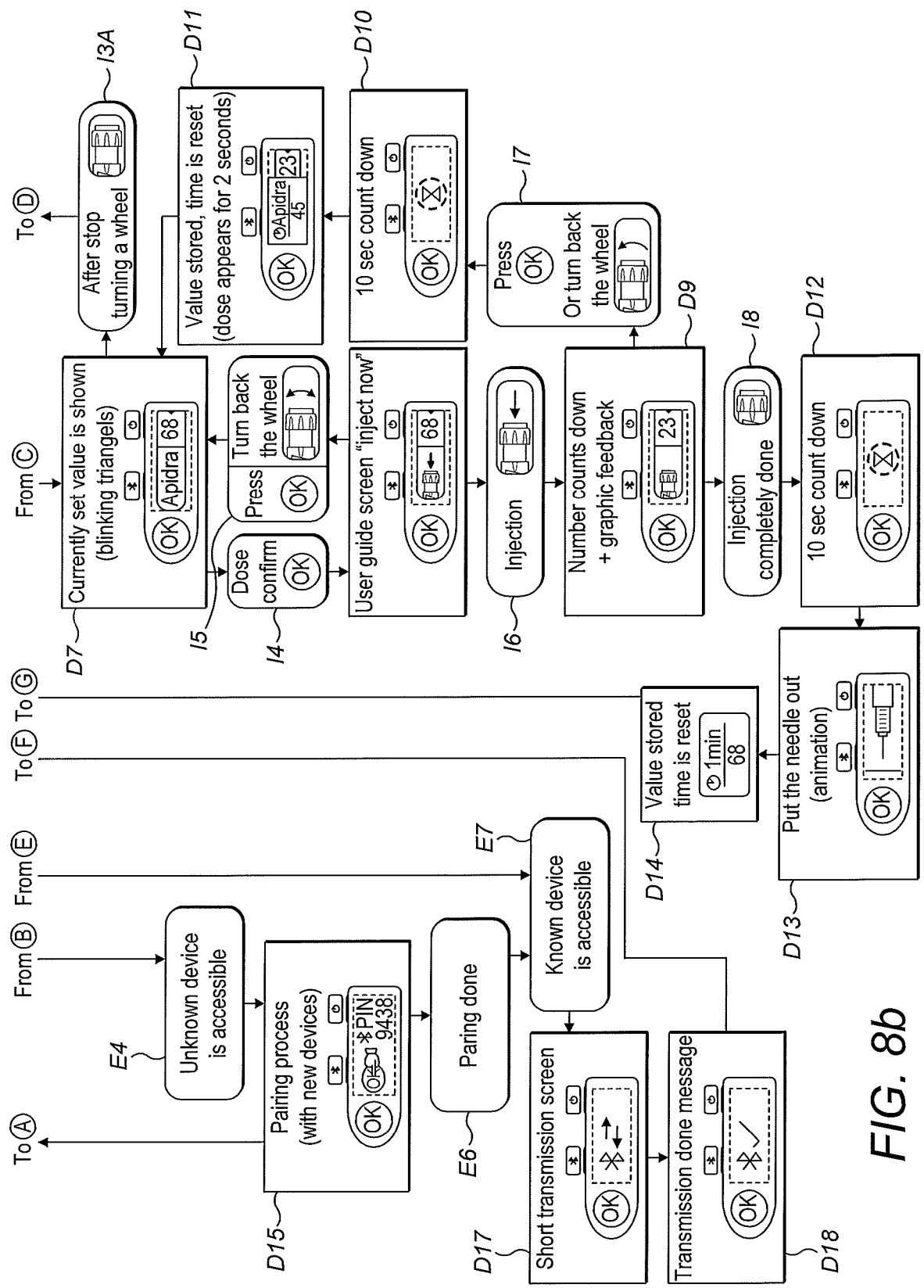
FIG. 8: a state diagram and flowchart illustrating operation of the device of FIG. 2b according to aspects of the invention.

FIG. 8 is a drawing that will now be used to illustrate operation of the supplemental device 2. FIG. 8 is part flowchart and part state diagram.

In the following, user inputs are denoted with reference numerals commencing "I", displays or states are denoted with reference numerals commencing with "D", and other elements of the drawing, for instance checks made by the supplemental device and explanatory information, are denoted by reference numerals commencing with "E".

In the following, the display 21 is referred to as the LCD 21, so as to avoid confusion between the hardware display 21 and the image that is displayed, and which may be termed a display. However, the LCD 21 may be any suitable form of display hardware.

Initially, the supplemental device is powered off. This provides the display shown in D1.

D1 also goes to show the general arrangement of the user interface features of the supplemental device. In particular, an uppermost surface of the supplemental device 2 is shown provided with the LCD 21 and the confirm/OK button 34. The confirm/OK button 34 is located to the left of the LCD 21 in this example, although it may have an alternative location in other embodiments. The button 22 and the communications button 33 are located on the side of the supplemental device 2. As shown here, the communications button 34 and the button 22 are located on the same side of the supplemental device 2, although in other embodiments the buttons are located differently. For instance, in some embodiments, the button 22 is located on the opposite side of the LCD 21 to the communications button 33. In some other embodiments, the communications button 33 and/or the button 22 are located on the top surface of the supplemental device 2.

At input I1, the user presses the button 22. The input I1 is detected by the supplemental device 2. In particular, the processor 24 detects that the button 22 has been pressed for a relatively short period. Other user inputs are detected by the supplemental device in a similar manner, and short hand explanation is occasionally provided in the following explanation. In the following, 'mode' and 'state' are used interchangeably to denote the same thing; if the supplemental device 2 is in mode X it means the same as it being in state X.

If when the supplemental device 2 is in the state illustrated in D1, the supplemental device 2 receives a long press of the button 22, denoted at input I2 in FIG. 8, the supplemental device 2 transitions to the state or display shown at D2. Here, a power on progress bar is displayed on the LCD 21. This progress bar includes a symbol denoting power or a battery and also includes an indicator relating to the power level of the battery. As shown in FIG. 8, the battery power is approximately one third of the full battery in this example. The supplemental device 2 remains in the state indicated by D2 for a predetermined time, for instance 2 or 3 seconds. Following the state indicated in D2, the supplemental device 2 transitions to one of four possible states.

If the supplemental device is not mounted on the injection device 1, as is detected by the supplemental device by the processor 24 examining a state of the detection switch 30, the supplemental device 2 transitions to the state indicated by D3 in FIG. 8. Here, the supplemental device provides on the LCD 21 a graphic indicating that no pen is present. This may be purely graphical, purely textural, or a combination of graphics and text.

If when the supplemental device 2 is in the state indicated by D2, the supplemental device 2 detects that there is not correct alignment between the supplemental device 2 and the injection pen 1, the supplemental device progresses to the state indicated by D4 in FIG. 8. An incorrect alignment between the supplemental device 2 and the injection device 1 may be detected by the supplemental device by examination of the symbols received by the OCR module 25 and/or the photometer 26.

Thirdly, if the supplemental device when in the state indicated by D2 detects that the battery 32 is almost empty, the supplemental device transitions to a low battery state indicated by D5 in FIG. 8. Here, a battery warning graphic is provided. This may take any suitable form.

If the supplemental device 2 does not transition into any of the three states indicated by D3, D4 and D5 in FIG. 8, it transitions to the state indicated by D6. This is called the default state. In the default state, the supplemental device indicates details of the last injection. Put another way, in the default state, the supplemental device 2 displays information relating to the last use of the injection pen 1.

The default state D6 is also arrived at following the unmounted state indicated by D3, the incorrect alignment state indicated by D4 or the low battery state indicated by D5. The supplemental device 2 may remain in any of these preceding states for a predetermined time, for instance 3 seconds, 5 seconds or 10 seconds, before transitioning to the default state, shown in D6.

In the case of the unmounted state indicated by D3, the supplemental device 2 may instead refrain from transitioning to the default state indicated by D6 until the supplemental device 2 detects that there is correct alignment between the supplemental device 2 and the injection pen 1. Alternatively, after the supplemental device has transitioned through the unmounted state indicated by D3, the supplemental device may remain in the default state indicated by D6 until the supplemental device detects, by examining the state of the detection switch 30, that the supplemental device 2 is mounted on the injection device 1.

With respect to the unaligned state indicated by display D4 in FIG. 8, the supplemental device 2 may remain in the unaligned state until the supplemental device 2 detects correct alignment between the supplemental device 2 and the injection device 1. Alternatively, the supplemental device 2 may transition from the unaligned state indicated by D4 to the default state indicated by D6 but refrain from progressing from the default state until the supplemental device 2 detects that there is correct alignment between the supplemental device 2 and the injection device 1.

If the supplemental device has transitioned through the low battery state indicated by D5 before arriving at the default state indicated by D6 in FIG. 8, the supplemental device 2 indicates periodically that there is a low battery state. This is achieved by a check step E1 that depends from the default state D6. The check step E1 involves the supplemental device 2 determining whether the battery 32 is almost empty and, if so, an action step E2 involves providing the warning shown in the display D5 periodically.

Even if the supplemental device 2 did not transition through the low battery state indicated by D5 before arriving at the default state indicated by D6, the check step E1 is performed periodically. Thus, when the supplemental device 2 is in the default state, indicated by D6 in FIG. 8, and the battery level falls such that at the check step E1 it is determined that the battery is almost empty, action step E2 involves causing the supplemental device 2 to transition to the low battery state indicated by D5.

Once the low battery state D5 has been transitioned through, the low battery display indicated by D5 is provided periodically until the battery 32 is replaced or otherwise replenished. In some embodiments, the low battery display indicated in D5 is provided only when the supplemental device 2 is in the default state. This prevents the low battery warning being provided to the user when the device is in use in connection with delivery of a dose of medicament and/or when the supplemental device 2 is attempting to communicate with another device.

Although not shown in FIG. 8, if when the supplemental device 2 is in the default state, indicated by D6 in the Figure, the supplemental device 2 receives a long press of the button 22, the supplemental device powers down. Thereafter, the device is in the off state that is indicated by D1 in FIG. 8. The supplemental device 2 may be responsive to a long press of the button 22 to power down from any state.

The supplemental device 2 may transition from the default state indicated by D6 in response to detecting that the user has turned the dosage dial 12. This is indicated at I3 in the Figure. In response, the supplemental device 2 enters a dosage dialling state, which is indicated at D7 in FIG. 8. Here, the supplemental device 2 displays on the LCD 21 the dose medicament that is currently dialled into the injection pen 1. This is known by the supplemental device 2 by virtue of reading of the FIG. 19 from the injection device by the OCR reader 25. In this state, the supplemental device 2 also displays an indication of the medicament that is present within the injection device 1. In the display D7, the medicament is indicated through the display of text that names the medicament, in this case "Apidra".

The currently set dose is indicated in the dosage dialling state in the display shown in D7 in any suitable way. The dose advantageously is indicated in the largest characters that can be accommodated by the LCD 21. In particular, the height of the letters may be equal to the height of the LCD 21, or at least have a height that is 80 or 90% or more of the height of the LCD 21. The supplemental device may provide the display D7 in such a way as to make it clear to the user that the dose value displayed on the LCD 21 relates to a dose that is currently dialled into the injection pen in any suitable way. For instance, graphical elements provided around the displayed dose value may blink or flash. Alternatively, the characters of the dose value themselves may blink or flash. Alternatively, the background may blink or flash.

When the supplemental device 2 detects that the dosage dial 12 has not been turned for a predetermined period, for instance 0.5 seconds or 1 second, this is detected at input I3a (although it is actually absence of an input) and the supplemental device 2 transitions to a dose dialled state, which is indicated by the dialled dose display D7a in FIG. 8. In the dose dialled state, the supplemental device 2 causes the LCD 21 to provide two different displays, with the device 2 transitioning from one display to the other display and back again on a periodic basis. In the dose dialled state indicated by D7a, both displays include the dialled dose, and this is provided in the same location. The dialled dose may be displayed in the same way in both of the displays. One display indicates the medicament that is present in the injection device 1. In this example, this is indicated by text that names the medicament, in this case "Apidra". The other display includes an indication that a dose of medicament may be delivered. In this example, this is provided by a graphic of a hand with a confirm/OK button.

If while in the dose dialled state illustrated by D7a the supplemental device 2 receives an input relating to further turning of the dosage dial 12, indicated by input I3 in FIG. 8, the supplemental device again proceeds to the dosage dialling state that is indicated by D7 in the Figure.

If the supplemental device 2 detects that the confirm/OK button 34 has been operated by a user when the device is either in the dosage dialling state indicated by D7 or in the dose dialled state indicated by D7a, this input 14 causes transition to an inject now state, which is indicated by D8 in FIG. 8. In the inject now state, a graphic is provided indicating to the user that injection is possible.

At this stage, the user has two options. They may change the dose. This is achieved by the user selecting the confirm/OK button 34 and then turning the dosage dialler 12. This is detected as an input 15 by the supplemental device. In detecting the input 15, the supplemental device 2 reverts to the dose dialled state indicated by D7 in FIG. 8.

Alternatively, the user can inject the medicament. This is detected by the supplemental device 2 as an input 16. Input 16 causes transition to a dosage delivery state, indicated as D9 in FIG. 8. Here, the dose remaining dialled into the injection device 1 is displayed on the LCD 21. As the dose is delivered, the dose remaining becomes smaller. As such, the remaining dose value counts down from the dialled in dose towards zero.

If the user does not deliver the entire dose, this is detected by the supplemental device at input 17 either by detecting depression of the confirm/OK button 34 or by detecting that the user has turned back the dosage dialler 12. The input 17 causes transition to a ten second countdown state, indicated at the display D10 in the Figure. After the ten seconds have lapsed, the supplemental device 2 transitions to a partial dose delivered state, indicated by a display D1l in FIG. 8. Here, the supplemental device 2 displays the dose delivered to the user through the injection pen 1. The dose delivered is equal to the dose that was dialled in, as detected by the supplemental device when in the dosage dialling state indicated by D7 or the dialled dose state indicated by D7a, minus the dose remaining when the input 17 was detected. In this state, the medicament that was delivered also is displayed. In this example, the delivered dose is indicated in characters that are smaller than the characters provided by either of the states indicated by D7 and D7a in FIG. 8. Arranged vertically with respect to the delivered dose is an indication of the medicament that was delivered. On transitioning to or from this state, a timer (not shown) within the supplemental device is reset. The timer allows the supplemental device 2 to calculate an elapsed time since a last dose was delivered. Transition from the state indicated by display D1l is to the state indicated by D7 in FIG. 8.

Alternatively, the supplemental device 2 may exit the dose delivery state indicated by D9 by detecting an input 18 indicative of the injection having been completed. In this case, the supplemental device transitioned to a countdown state that is indicated by the display D12 in FIG. 8. Here, the LCD 21 is provided with an icon that is the same as the icon provided in the display of the countdown state indicated by D10 in the Figure.

After ten seconds have elapsed, the supplemental device 2 transitions to a remove needle instruction state, indicated at the display D13 in FIG. 8. Here, the supplemental device 2 provides a graphic that indicates to the user that the needle of the injection device 1 should be replaced. After a predetermined time, or upon detecting that the needle has been replaced if the acoustical sensor 27 is present, the supplemental device 2 transitions to a reset state that is indicated by the display D14 in FIG. 8. Here, the value of the delivered dose is stored in the supplemental device 2 and a timer (not shown) is started. The timer provides a value that is indicative of the time elapsed since the last dose. After the reset state, the supplemental device 2 transitions to the default state, indicated by D6 in FIG. 8.

If when the supplemental device 2 is in the default state, indicated by D6, it detects an input 19 indicating that the user has pressed the communication button 33, it transitions from the default state. Here, the supplemental device 2 determines whether a device is accessible. A device here is for instance the blood glucose measurement unit 42. If a determination at step S3 indicates that a device is accessible and it is determined in E4 that the device is unknown, the supplemental device 2 enters a pairing process state, which is indicated by D15 in the Figure. In this state, the supplemental device 2 initiates pairing with the detected device. In the case of the wireless unit 28 being a Bluetooth transceiver, this involves initiating pairing in accordance with the Bluetooth standard. In the pairing process state, indicated by D15, a Bluetooth PIN number is displayed on the LCD 21. This is accompanied with an icon requesting that the user confirm that the PIN number matches with one displayed on the unknown device. If the supplemental device 2 determines at E5 that pairing has failed, the supplemental device 2 transitions to a Bluetooth error message state, indicated by D16 in the Figure. This state is also transitioned to following input 19 if it is determined at E8 that no device is accessible. In the Bluetooth error message state, indicated by D16, an icon is displayed on LCD 21 indicating that no communication is possible. Following the Bluetooth error message state, for instance after a predetermined time, the supplemental device 2 transitions to the default state, indicated by D6.

If in the pairing state the supplemental device at E6 determines that pairing has been completed, it transitions to a short transmission state, indicated by D17. The supplemental device also transmissions to the short transmission state indicated by D17 from the default state indicated by D6 following input 19 if the supplemental device determines that a device is accessible at E3 and at E7 determines that it is a known device.

In the short transmission state, indicated by D17, an icon or graphic is displayed on the LCD 21 indicating that communication is in process. Once communication is complete, the supplemental device 2 transitions to a transmission done stage, indicated by D18. Here, the supplemental device 2 provides a graphic indicating that transmission has been completed. Following the transmission done state, the supplemental device 2 transitions to the default state, indicated by D6.

When in the default state, indicated by D6, operation is as follows. The supplemental device 2 is expected to be in the default state for most of the time for which it is powered on. As such, the displays D6 when in the default state are the displays that are likely to be seen most by a user of the supplemental device.

When in the default state, the supplemental device is configured to indicate to the user details of the last delivered dose. The details include the quantity of the dose and the time elapsed since the last dose delivery. These details also include the identity of the medicament.

In these embodiments, this is achieved by transitioning between two different displays in the default state. The first display is shown uppermost in display D6 in FIG. 8. Here, it will be seen that there are two regions of the LCD 21. A region on the left side occupies approximately two thirds of the area of the display. This region is hereafter termed the last dose region. On the right side of the LCD 21, to the right of the last dose region, is another region. The other region in this example displays a dose that is dialled into the injection pen 1. The information displayed on the right side of the LCD 21 is the dialled value from the injection pen 1. This is not influenced by the information displayed on the left side of the LCD 21.

The last dose region in the first display, shown uppermost in D6 in FIG. 8, is divided into two areas. Here, they are upper and lower areas. In a first area, here the lower area, the last delivered dose is displayed. This is in the form of a number, indicating the dose in IUs.

In the second area, the elapsed time since the last dose delivered is displayed. Here, this is displayed as a time expressed as a number and with a unit of time expressed in Roman characters. Display of the unit of time allows a user to distinguish between the display of the time since the last dose and the quantity of the dose. The second area also includes a graphic indicating a timer or clock, which reinforces this message.

In the second display, shown lowermost in D6 in FIG. 8, the first area is unchanged. The first area thus displays the quantity of the last dose. The second area does not show the time elapsed since the last dose. Instead, it shows the medicament of the last dose. Here, this is indicated by text that spells the name of the medicament, in this case "Apidra". The clock or timer icon is again displayed in the second area.

In the default state, the supplemental device 2 causes the display to transition between the first and second displays, shown uppermost and lowermost respectively, periodically. Transitioning may occur every two seconds, for instance.

As can be seen in FIG. 8, the first area of the dose display region 21B is larger than the second area. As such, the height of the characters used to indicate the quantity of the dose are larger than the characters used to indicate the time elapsed since the last dose or the identity of the medicament. As such, a user is able to determine quickly and easily, perhaps with only a glance, the quantity of the last dose.

Additionally, the user is able to determine relatively easily the time elapsed since the last dose. It is the time elapsed since the last dose and the quantity of the dose that are the parameters that are most of interest to users of medicaments that are used to treat diabetes. It is these parameters that are most of interest to the user when determining the next dose of medicament, in terms of the time when it should be delivered and in terms of the quantity of medicament that may be needed.

As such, the provision of the default state and the displays provided in that state by the supplemental device 2 can allow the user better to treat the condition for which the medicament is prescribed. Put another way, the features of the supplemental device when in the default state can allow the user more easily to treat their condition, potentially providing better treatment for the user.

An alternative embodiment will now be described with reference to FIGS. 2c and 9.

As can be seen in FIG. 2c, the supplemental device 2 is provided with a LCD 21 and a button 22. The LCD 21 is a touch-sensitive display, through which a user can provide input to the supplemental device. As such, the touch-sensitive LCD 21 also provides the functions provided by the communications button 33 and the confirm/OK button 34 in the embodiment of FIG. 8 and FIG. 2b.

Operation of the supplemental device according to this embodiment is quite similar to the operation of the device of FIG. 2b, as described with reference to FIG. 8. In FIG. 9, reference numerals are retained from FIG. 8 for like elements, and only the differences between operation of the embodiment of FIG. 2c and the embodiment of FIG. 2b will be described here. For features and operation of the device of FIG. 2c that are the same as features and operations of the device of FIG. 2b and FIG. 8, no discussion is made in the following.

Figure 9A:
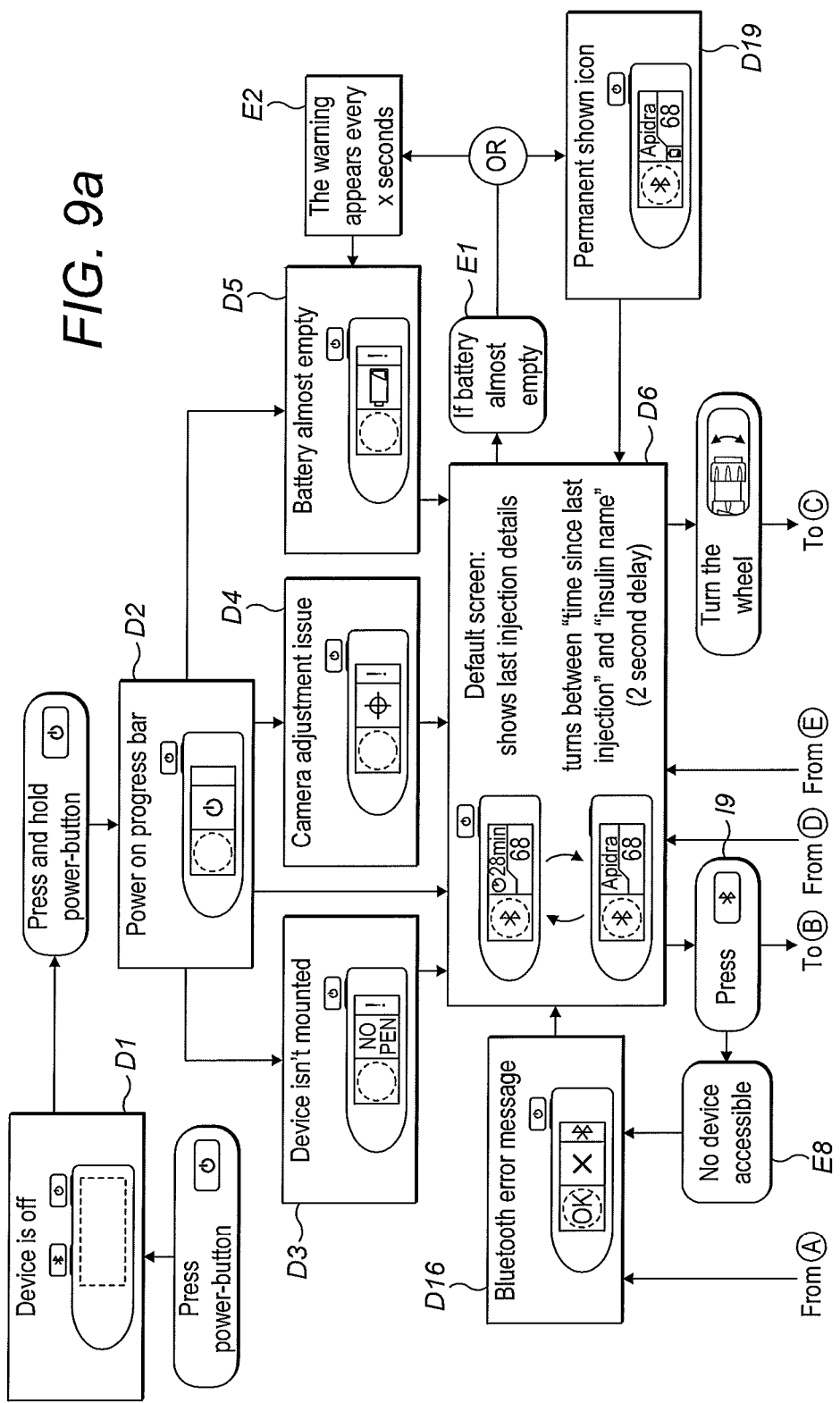
FIG. 9: a state diagram and flowchart illustrating operation of the device of FIG. 2c according to aspects of the invention.
Figure 9B:
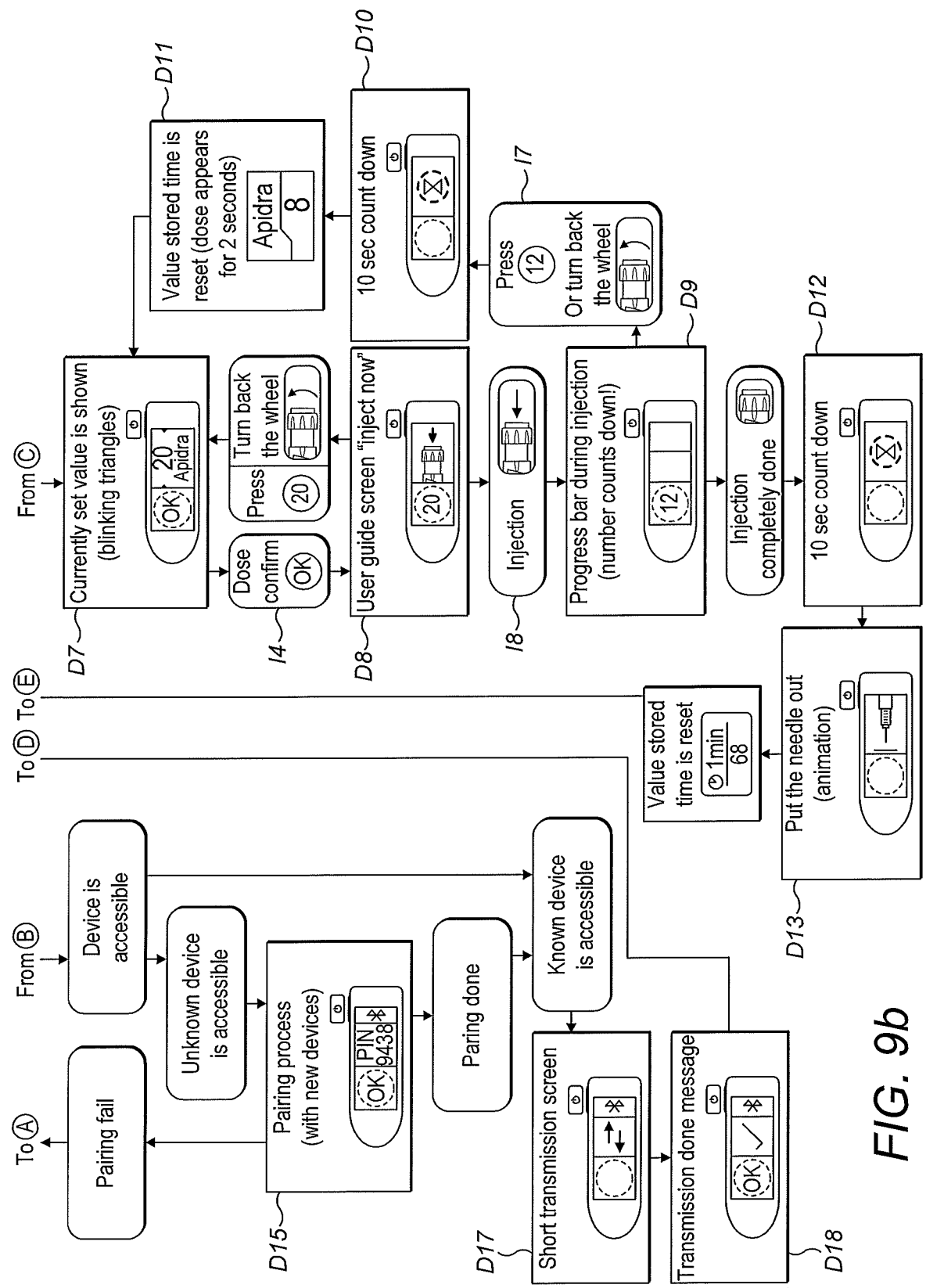

The device off state, illustrated by display D1 in FIG. 9 is very similar to the corresponding state of the device operation shown in FIG. 8. This display D1 illustrates the overall layout provided on the LCD 21. In particular, a first region 21B of the display is a display region 21B. This is shown on the right of the display of D1 of FIG. 9. A second region 21A of the display is an input region 21A. This is shown on the left in D1. The input region 21A is also an active display region 21B. However, the input region 21A is a region where user inputs may be received. The input region 21A includes a display of a virtual button at appropriate times, in particular when the supplemental device 2 is in certain states. The input region 21A in this embodiment is always located in the same place on the LCD 21. This simplifies the experience for the user. In other embodiments, the input region 21A may change in location depending on the state of the supplemental device. The input region 21A is the touch sensitive input 35 shown in FIG. 2c.

In the device off state shown in D1, the LCD 21 is blank. When the LCD 21 is blank in a region, nothing is displayed in that region. When the input region 21A is blank, an outline of the virtual button may be displayed, although nothing is displayed within the virtual button.

In the power off progress state shown by D2, the input region 21A is left blank, that is nothing is displayed in the input region 21A. In this state, the display region 21B is provided with an indicator that indicates the amount of power remaining in the battery 32. This indicator is the same as the indicator shown in D2 of FIG. 8, although it is smaller in size.

In the device not mounted state D3, the input region 21A is blank, and a graphic indicating that the pen is not connected is shown in the display region 21B. In the camera adjustment issue state shown at D4, the input region 21A is left blank and the display region 21B indicates that there is not alignment between the supplemental device 2 and the injection device 1. In the battery low state indicated by display D5, the input region 21A is left blank and the display region 21B includes an icon indicating that the battery is almost empty.

In the default state, the input region 21A is provided with an icon relating to communication options. In this example, the input region 21A is provided with an icon indicating a Bluetooth communication option. The supplemental device 2 is configured when in the default state to respond to a user input 19 comprising touching of the LCD 21 at the input region 21A to proceed through the checks E3 and E8, as described above with reference to FIG. 8.

When in the default mode, the display region 21B of the display is provided with the displays as described above in relation to the first region of the display in the default state of FIG. 8.

If the supplemental device 2 detects that the battery is almost empty when the device is in the default state shown by D6, the check E1 may cause an action E2 which results in transitioning of the device to the battery almost empty state, providing a display shown in D5, periodically. Alternatively, the supplemental device 2 may be configured to include a low battery icon within the display region 21B. This is indicated by the display D19 in FIG. 9.

When in the currently set value state indicated by the display D7 in FIG. 9, the currently dialled dose is displayed in the display region 21B. The input region 21A is provided with a graphic, which in this case is the word "OK". When in this mode, the supplemental device 2 is responsive to detection of a user input at the input region 21A of the LCD 21, represented by input 14 in FIG. 9, to transition to the inject now state, illustrated by display D8 in FIG. 9. In the inject now state, the input region 21A is provided with an indication of the dialled dose. The display region 21B is provided with an icon which is the same as the icon shown in D8 of FIG. 8. After an injection input 18, the number displayed within the input region 21A counts down, reflecting the remaining dialled dose.

The supplemental device 2 is responsive to detection of a user input at the input region 21A of the LCD 21, indicated by input 17 in FIG. 9, to transition to the countdown state indicated by D10 in the Figure.

In the display indicated by display D1l in FIG. 9, the delivered dose is displayed, along with an indication of the medicament delivered.

In the countdown states indicated by the displays D10 and D12 in FIG. 9, the input region 21A of the LCD 21 is left blank. This is the case also for the remove needle state instruction provided by D13 in FIG. 9. In these states, no transition occurs from user input, so it is appropriate for the input region 21A of the LCD 21 to remain blank.

The communication error message state, indicated by D16, is similar to the corresponding display of FIG. 8. However, the input region 21A of the LCD 21 includes the text "OK". The supplemental device 2 is configured to transition from the communication error message state shown by D16 to the default state shown by D6 after a predetermined time or upon detecting a user input at the input region 21A of the LCD 21.

The text "OK" is provided at the input region 21A of the LCD 21 also when in the pairing state, indicated by display D15 in FIG. 9. The supplemental device 2 is configured to respond to detection of a user input at the input region 21A of the LCD 21 to transition either to the communication error message state shown by D16 or the short transmission state indicated by D17 depending on whether pairing has been achieved. Alternatively, transitioning may occur automatically, for instance in response to detection of a time out.

It will be appreciated from the above description of FIG. 9 that operation of the supplemental device of FIG. 2c is quite similar to the operation of the device of FIG. 2b. However, the dynamic adjustment of the text or graphics control to be displayed in the input region 21A of the LCD 21 simplifies the process of use for the user. In particular, aside from the button 22, there is only ever one input button/region 21A that needs to be operated by the user. Moreover, the consequence of the user operating the input should be more obvious.

Additionally, the arrangement of the supplemental device 2 of FIG. 2c is such that the user cannot operate the communications button other than when the device is in the default state, indicated by D6. This prevents the user believing that the supplemental device 2 might lead to actuation of the communications button 33 other than when in the default state, shown by D6.

It will be appreciated that the above-described embodiments are merely examples and that numerous alternatives will be envisaged by the skilled person and are within the scope of the present invention.

For instance, the communication states etc may be replaced by alternative states in which operation of the supplemental device 2 is quite different, or these states may be omitted altogether.

Figure 10:
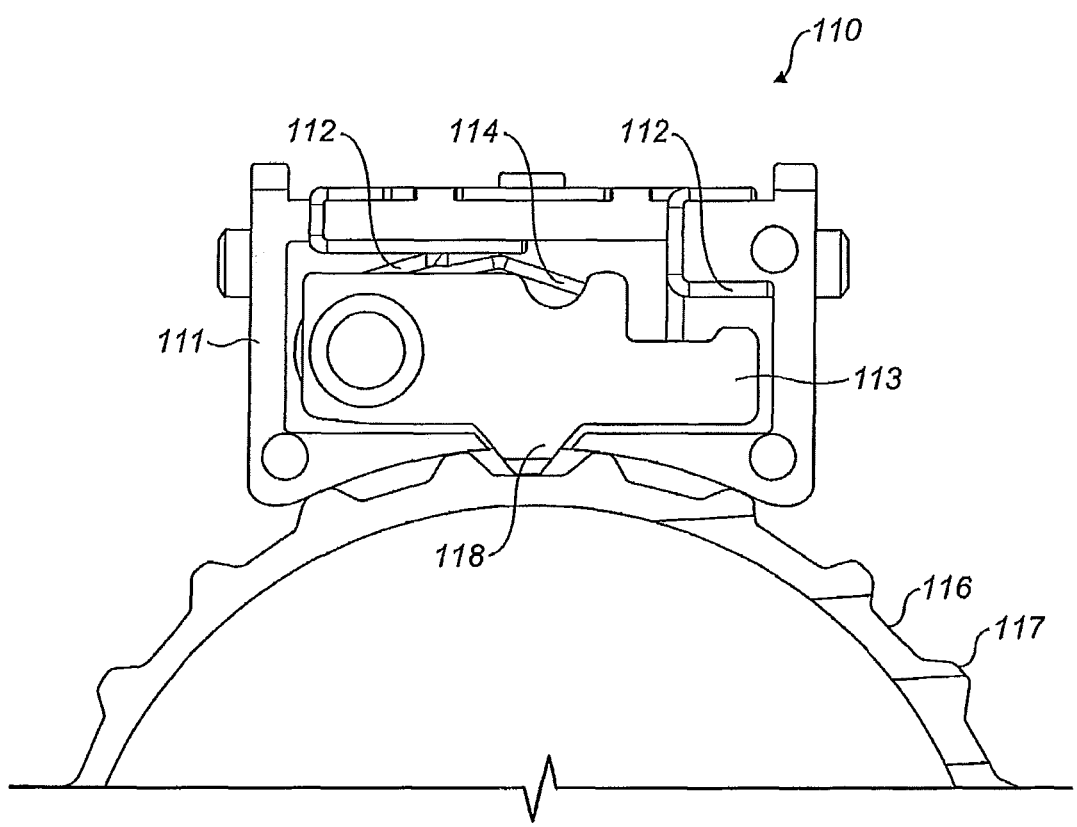
FIG. 10: a lateral cross-section taken through the injection device with a supplemental device attached.
Figure 11:
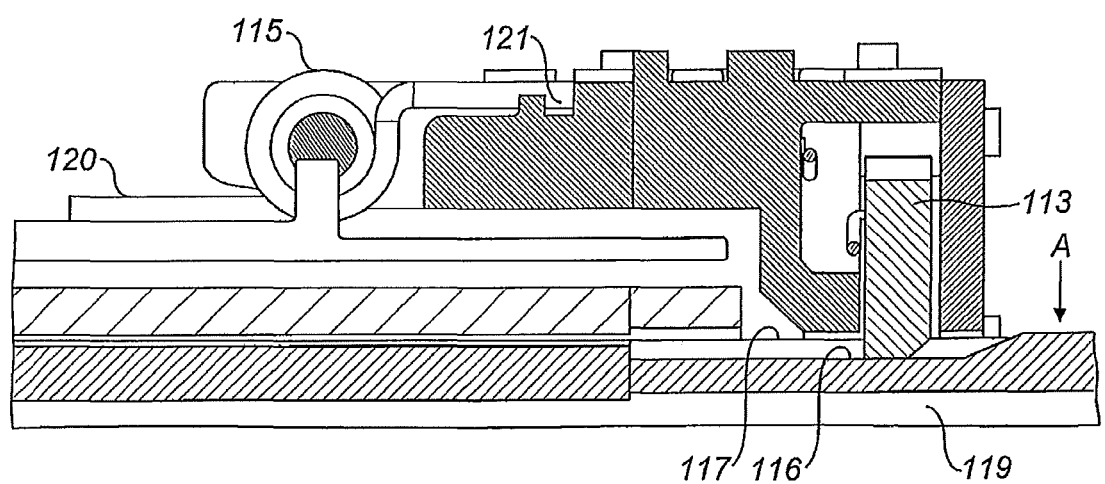
FIG. 11: an axial cross-section taken through the injection device with a supplemental device attached.

Referring to FIGS. 10 and 11, embodiments of the invention will now be described. FIG. 10 shows a lateral cross-section taken through the injection device 1 with supplemental device 2 attached. In FIG. 10, only the central part of the supplemental device 2 is shown; the mating unit which embraces the injection device 1 is omitted for clarity. FIG. 11 shows an axial cross-section taken through the injection device 1 with supplemental device 2 attached. Some components of the supplemental device are omitted or shown in wireframe in FIG. 11 for clarity.

FIGS. 10 and 11 both show an electromechanical switch arrangement 110. In FIG. 10, the remained of the supplemental device 2 is not shown. The electromechanical switch arrangement 110 comprises a self-contained unit which is fitted to the supplemental device 2. The electromechanical switch arrangement 110 may for example be housed in a recess in the underside of the supplemental device 2 (the part which contacts the injection device 1). The electromechanical switch arrangement 110 may be secured to the supplemental device 2 by friction or by an interlocking arrangement (not shown), or alternatively by screws, adhesive or the like.

The electromechanical switch arrangement 110 comprises a main body 111 (also referred to herein as a housing 111). A cavity is defined inside the main body 111. An upper part of the main body 111 is arranged to engage with the housing 20 of the supplemental device 2 to secure the electromechanical switch arrangement 110 to the supplemental device 2. A lower part of the main body is concave in shape and matches the curvature of the injection device 1. The lower part of the main body 111 has an aperture.

In embodiments of the invention, the injection device 1 to which the supplemental device 2 is to be attached has a corrugated dialling sleeve 119. The corrugations are defined by troughs 116 and crests 117. The dialling sleeve 119 is configured to rotate with the dosage knob 12 during dose dialling. The dialling sleeve 119 may be coupled directly to the injection button 11. The lower part of the main body 111 of the electromechanical switch arrangement 110 abuts several of the crests 117 of the corrugated dialling sleeve 119 but the dialling sleeve 119 is free to rotate relative to the electromechanical switch arrangement 110.

A switch 113 (also referred to as a protrusion, a switching member or switching lever) is rotatably mounted inside the main body 111 of the electromechanical switch arrangement 110. The switch 113 has a protrusion 118 and is arranged such that this protrusion passes through the aperture in the main body 111 and protrudes from the main body 111. An internal spring 114 biases the switch 113 towards the position shown in FIG. 10, in which the switch 113 abuts an internal surface of the main body 111 and the end of the protrusion 118 abuts a trough 116 of the dialling sleeve 119. The internal spring 114 may for example be a torsion spring. In some embodiments, the injection device 1 is configured such that a small portion of the dialling sleeve 119 adjacent the dosage button 12 extends out of the housing 10 of the injection device 1 when no dose has been dialled. This allows the protrusion 118 to contact the dialling sleeve 119 at all times during operation of the device.

The inner wall of the electromechanical switch arrangement 110 comprises two electrical contacts 112. These contacts are arranged to be engaged by corresponding electrical contacts on the switch 113. In some embodiments, the contacts 112 and/or the corresponding contacts on the switch 113 are sprung contacts. For example, a first of the contacts 112 may be engaged at all times by a contact on the switch. A second of the contacts 112 is not engaged by the switch 113 when in the position shown in FIG. 10. This second contact 112 is engaged by the switch 113 only when the protrusion 118 of the switch 113 rides up a crest 117 of the dialling sleeve 119, causing the switch to rotate within the main body 111. When the switch 113 engages this second contact, an electrical connection is made through the switch between the two contacts 112. As previously described, the supplemental device 2 comprises a processor 24. This processor 24 is configured to control the application of a signal to one of the contacts 112 and to detect when the circuit is completed by measuring a signal at the other of the contacts 112.

The supplemental device 2 may also comprise a compensation spring 115 (also referred to herein as a biasing member), visible in FIG. 11. The compensation spring 115 forms part of the supplemental device 2, but is external to the electromechanical switch arrangement 110. The compensation spring 115 may be a torsion spring. The compensation spring 115 has a first end 120 which is secured internally to the housing 20 of the supplemental device 2. The concave underside of the supplemental device 2 is shown in wireframe in FIG. 11. The compensation spring 115 has a second end 121 which is secured to the electromechanical switch arrangement 110. The second end 121 of the compensation spring 115 may be secured to an upper part of the electromechanical switch arrangement 110 (relative to the orientation of shown in FIG. 11). The compensation spring 115 exerts a force on the electromechanical switch arrangement in the direction of the arrow "A" on FIG. 11. This force causes the electromechanical switch arrangement 110 to be biased towards the injection device 1 and in particular towards the dose dialling sleeve 119.

The compensation spring 115 may compensate for relative movement between the supplemental device 2 and injection device 1 and/or between the electromechanical switch arrangement 110 and supplemental device 2 as described in greater detail below. These relative movements may be due to manufacturing tolerances of the supplemental device 2, electromechanical switch arrangement 110 and injection device 1, in particular the dose dialling sleeve 119, or may be an intentional design feature. In some other embodiments, the compensation spring 115 is not present.

Exemplary operation of the injection device 1 and supplemental device 2 containing the electromechanical switch arrangement 110 will now be described.

First the electromechanical switch arrangement 110 is secured to the supplemental device 2. This may be done during manufacture of the supplemental device 2. Alternatively, the electromechanical switch arrangement 110 may be an integral part of the supplemental device 2. A user then fits the supplemental device 2 to the injection device 1 as previously described. Once the supplemental device 2 has been fitted to the injection device 1, the lower part of the electromechanical switch arrangement 110 abuts the surface of the injection device 1.

When a dose has been dialled into the injection device 1, the electromechanical switch arrangement 110 abuts the dose dialling sleeve 119, as depicted in FIGS. 10 and 11. The concave underside of the electromechanical switch arrangement 110 contacts several crests 117 of the corrugated surface of the dialling sleeve 119. The dose dialling sleeve 119 has a smaller diameter than the outer housing 10 of the injection device 1 and may have the same or a smaller diameter than the dosage knob 12.

Due to the action of the internal spring 114, the protrusion 118 of the switch 113 is forced to protrude through the aperture in the main body 111 of the electromechanical switch arrangement 110. Thus the protrusion 118 may contact a trough 116 of the dose dialling sleeve 119 while the electromechanical switch arrangement 110 rests on the crests 117 of the sleeve.

A user then dials in a dose by grasping and rotating the dosage knob 12. The dose dialling sleeve 119 rotates relative to the supplemental device 2. As the sleeve 119 rotates, the protrusion 18 of the switch 113 follows the contours of the dialling sleeve surface. When a crest 117 is rotated past the aperture, the protrusion 118 rides up the crest, forcing the switch 113 to rotate within the main body 111. The switch 113 contacts the second of the contacts 112 when the protrusion 118 reaches the top of a crest 117. The switch 113 may be in contact with the first of the contacts 112 at all times. An electrical path is formed between the two contacts 112 when the switch 113 engages with the second of the contacts 112. The processor 24 detects that the switch has been closed by applying a signal at the first contact and measuring a signal at the second contact.

As the sleeve continues to rotate, the protrusion 118 rides down the crest 117 and into the next trough 116 under action of the internal spring 114. The switch 113 ceases to contact the second contact 112. The processor 24 determines from this sequence that one unit (IU) has been dialled into the injection device 1. For each unit which is dialled into the injection device 1, the processor detects one connection of the circuit preceded and followed by a disconnection.

The switching point of the electromechanical switch arrangement 110, i.e. the point at which the switch 113 completes a circuit between the two contacts 112, occurs when the protrusion 118 rides up to the top of a crest 117. The contacts 112 may be sprung contacts to allow some range in the switching point.

The user then delivers the selected dose. During this procedure, the dose dialling sleeve 119 moves back into the injection device 1, but does not rotate. The dose dialling sleeve 119 is disconnected from the sleeve 19 and dosage knob 12 by an internal clutch coupled to the injection button 11. Alternatively, the dose dialling sleeve 119 may be coupled directly to the injection button, which is itself disconnected from the sleeve 19 and dosage knob 12 by the internal clutch. Thus during dose delivery, the protrusion 118 of the switch 113 remains in the same trough 116 of the dose dialling sleeve 119 and no circuit connection is made by the switch 113.

The electromechanical switch arrangement 110 may be provided in addition to the OCR reader 25, although the OCR reader is an optional feature. If the processor 24, using the OCR reader 25, detects that the numbers on the sleeve 19 are changing, it may be necessary also to determine whether a dose is being dialled in (dose setting), dialled out (dose correction) or delivered (dose dispense). This determination is not possible using the OCR reader 25 alone. Use of the electromechanical switch arrangement 110 allows this determination to be made.

If the processor 24 determines that the numbers detected by the OCR reader 25 are increasing and also that the electromechanical switch arrangement 110 is being alternately opened and closed, it can be deduced that a dose is being dialled into the injection device 1. If the processor 24 determines that the numbers detected by the OCR reader 25 are decreasing and also that the electromechanical switch arrangement 110 is being alternately opened and closed, it can be deduced that a dose is being dialled out of the injection device 1, without being delivered. If the processor 24 determines that the numbers detected by the OCR reader 25 are decreasing and also that no connection is made in the electromechanical switch arrangement 110, it can be deduced that a dose is being delivered.

The switch 113 is described above as rotationally mounted. However, it may instead move in another way within the electromechanical switch arrangement 110, for example by sliding vertically. The internal spring 114 may be disposed in the centre of the switching member to bias it towards the aperture in the main body 111. The compensation spring 115 may alternatively be a coil spring or another type of biasing means. Instead of being located adjacent to the electromechanical switch arrangement 110, the compensation spring 115 may be located above the electromechanical switch arrangement 110, for example in a cavity between the housing 20 of the supplemental device 2 and the main body 111 of the electromechanical switch arrangement 110. The switch 110 is described as being closed when the protrusion 118 ascends a crest of the corrugated dialling sleeve 119 or when the protrusion ascends the axial ramp 122 and open at all other times. However, the switch 110 may alternatively be opened when the protrusion ascends a corrugation or the axial ramp 122 and closed at all other times. Thus the processor may detect either state (or sense) change in the switch 110 and interpret this change as described above.

In some embodiments, the electromechanical switch arrangement 110 may be used to determine that a dose has been completely delivered, i.e. as a "dispense-end switch". As can be seen in FIG. 11, each trough 116 of the dose dialling sleeve 119 ends at the dosage knob 12 end with an axial ramp 122. During dispensing, the switch 113 remains in a trough 116 of the dose dialling sleeve 119 such that the state of the electromechanical switch arrangement 110 does not change. As the dose dialling sleeve moves from a one unit dose position to a zero unit dose position, the switch 113 ascends this axial ramp 122. In this position, the electromechanical switch arrangement 110 has a different state to when the switching member is in a trough 116 of the dose dialling sleeve 119. In other words, in all integer unit dose positions the electromechanical switch arrangement 110 has a first state (e.g. an open state), but when in a zero dose position the electromechanical switch arrangement 110 has a second state (e.g. a closed state). The processor 24 may then control the supplemental device 2 to enter a "dispense-end" mode and control the display 21 to show an appropriate screen.

If the electromechanical switch arrangement 110 remains in this second state for a predetermined length of time, the processor 24 may determine that a dose dispense has been completed. Optionally, the processor 24 may place the supplemental device 2 into a power conserving "sleep mode" after this (or a longer) predetermined time. The supplemental device 2 may be woken from a sleep mode when a new dose is dialled into the injection device 1 and the state of the electromechanical switch arrangement 110 changes.

In the above described embodiments, the same switch 113 which contacts the crests 117 and troughs 116 of the dose dialling sleeve 119 is also used to determine when the dose dialling sleeve 119 reaches a zero unit dose position. An advantage of these embodiments is that detection of a completed dose can be accomplished without modification to the existing electromechanical switch arrangement 110. If the detection of a completed dose is used as a trigger to place the supplemental device 2 into a sleep mode, then the overall power consumption of the device is reduced. This may be particularly beneficial when the supplemental device 2 contains power heavy components, such as an OCR system.

Figure 12:
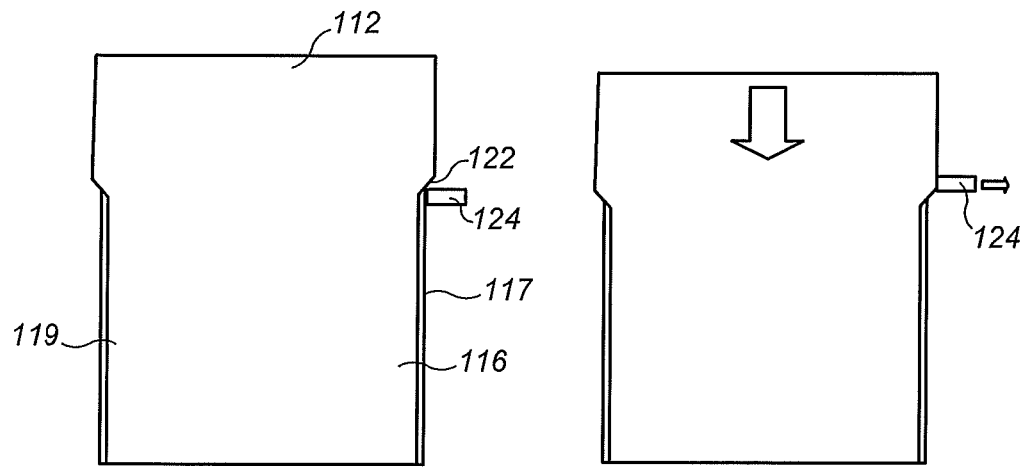
FIGS. 12 and 13: schematic diagrams showing two positions of a switching member relative to an injection device according to aspects of the invention.

FIG. 12 shows schematically another embodiment of the invention in which another switching member 124, being part of a second electromechanical switch (not shown), is used as the "dispense-end" detection switch. The first switch 113 is used as previously described to contact the dose dialling sleeve 119 at all times during rotation and is omitted from FIG. 12.

The second electromechanical switch (not shown) may be housed within the electromechanical switch arrangement 110 or alternatively may be part of a second electromechanical switch arrangement. In either case, the second switching member 124 protrudes from the underside of the supplemental device 2, but is not biased against the surface of the dose dialling sleeve 119. It does not therefore move into the troughs 116 of the dose dialling sleeve. The switching member 124 may contact the crests 117 of the dose dialling sleeve 119 as the dialling sleeve is rotated, but this contact does not cause the second switch to change state. The second switching member 124 may contact the dose dialling sleeve 119 at a different circumferential position to the first switch 113 and/or be offset axially with respect to the first switch 113.

FIG. 12 shows two positions of the second switching member 124 relative to the dose dialling sleeve 119. The first position represents the arrangement when a dose of one unit is dialled into the supplemental device 2. In this position the second electromechanical switch arrangement has a first state (e.g an open state). When the last unit dose is delivered (indicated by the arrow in FIG. 12), the second switching member 124 ascends the axial ramp 122 and the state of the second electromechanical switch arrangement changes to a second state (e.g. a closed state) as shown in the second position in FIG. 12. The change in state of the second switch only occurs when the dialled dose is decreased from one to zero. The processor 24 may detect the change in state of the second switch and determine that a dose of zero units is dialled into the device. The first switch 113 may also ascend the ramp 122 or may be positioned such that it does not ascend the ramp 122.

As the second electromechanical switch arrangement changes state only when the second switching member 124 ascends the ramp 122 at the end of the dose dialling sleeve 119, the second switch acts as a reliable means of determining when a dose has been fully delivered. Detection that a dose has been fully delivered may be used to activate a power saving or sleep mode as previously described or to trigger another function of the supplemental device 2, such as displaying the dose that has been delivered on the display 21 of the supplemental device 2 and/or triggering communication of data stored in the supplemental device 2 with an external apparatus.

Figure 13:
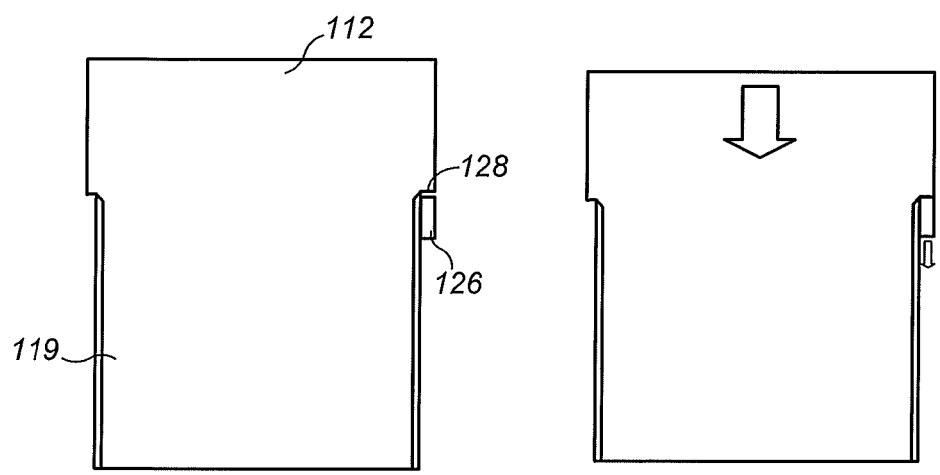

FIG. 13 shows schematically a further embodiment of the invention in which another switching member 126, being part of a second electromechanical switch (not shown), is used as the "dispense-end" detection switch. The first switch 113 is again omitted from FIG. 13. The embodiment shown in FIG. 13 is similar to that shown in FIG. 12 except that the switching member 126 is movable in an axial direction, rather than in a radial direction. The skilled person will appreciate that the internal construction of the second electromechanical switch may be modified to accommodate this axial movement. For example, the switching member 126 may contact a cam or be connected to a rotatable or hinged arm or actuator within the switch arrangement in order to cause the state of the switch to change.

The switching member 126 does not contact the troughs 116 or crests 117 of the dose dialling sleeve 119. Alternatively, the switching member 126 may slide across the crests 117 of the dose dialling sleeve 119. The switching member 126 is contacted by the dose dialling sleeve 119 and moved only when the dose dialling sleeve 119 moves from a one unit dose position to a zero unit dose position. In the embodiment of FIG. 13, the dose dialling sleeve 119 does not require an axial ramp, but could instead comprise a flange 128. A surface of the dosage knob 112 where it meets the dose dialling sleeve 119 may act as the flange 128 or alternatively the flange may comprise a separate ring of material having a larger diameter than the dose dialling sleeve 119.

FIG. 13 shows two positions of the switching member 126 relative to the dose dialling sleeve 119. The first position represents the arrangement when a dose of one unit is dialled into the supplemental device 2. In this position the second electromechanical switch arrangement has a first state (e.g an open state). When the last unit dose is delivered (indicated by the arrow in FIG. 13), the flange 128 abuts the switching member 126 causing it to move as shown in the second position in FIG. 13. The state of the second electromechanical switch arrangement changes to a second state (e.g. a closed state). The change in state of the second switch only occurs when the dialled dose is decreased from one to zero. The processor 24 may detect the change in state of the second switch and determine that a dose of zero units is dialled into the device.

As the second electromechanical switch arrangement changes state only when the switching member 126 is caused to move, the second switch acts as a reliable means of determining when a dose has been fully delivered. Detection that a dose has been fully delivered may be used to activate a power saving or sleep mode as previously described or to trigger another function of the supplemental device 2, such as displaying the dose that has been delivered on the display 21 of the supplemental device 2 and/or triggering communication of data stored in the supplemental device 2 with an external apparatus.

The invention claimed is:

1. A supplemental device for attachment to an injection device, the supplemental device comprising:
    an electromechanical switch arrangement having an open state and a closed state, wherein in the open state two electrical contacts of the electromechanical switch arrangement are electrically isolated from each other, and in the closed state the electromechanical switch arrangement provides a conductive path between the two electrical contacts, the electromechanical switch arrangement comprising:
        a main body; and
        a protrusion configured to protrude from the main body such that the protrusion contacts a surface of the injection device in a zero unit dose position of the electromechanical switch arrangement, wherein the open state or the closed state of the switch arrangement is configured to change, during dose dialing, when a dose dialed into the attached injection device moves the electromechanical switch arrangement from a one unit dose position to the zero unit dose position; and
    a processor arrangement configured to:

detect one or more changes in the open state or the closed state of the electromechanical switch arrangement;

determine from the one or more changes in the open state or the closed state that the dose dialed into the injection device, during dose dialing, has moved the electromechanical switch arrangement from the one unit dose position to the zero unit dose position; and in response to determining from the one or more changes in the open state or the closed state that the dose dialed into the injection device has moved the electromechanical switch arrangement from the one unit dose position to the zero unit dose position, change a display output of the supplemental device from a dose delivery display to a dispense-end display.

2. The supplemental device according to claim 1, wherein the protrusion is further configured to contact the surface of the injection device when any number of dose units are dialed into the injection device.

3. The supplemental device according to claim 1, wherein the protrusion is further configured to contact the surface of the injection device only in the zero unit dose position, wherein the surface of the injection device is a raised surface.

4. The supplemental device according to claim 1, wherein the processor arrangement is further configured, subsequent to determining from the one or more changes in the open state or the closed state of the electromechanical switch arrangement that the electromechanical switch arrangement is in the zero unit dose position, to place the supplemental device into a power saving mode.

5. The supplemental device according to claim 1, wherein the supplemental device further comprises a dose dialed detector operable to detect a dose of medicament dialed into the attached injection device.

6. The supplemental device according to claim 5, wherein the dose dialed detector comprises an image capture device and an optical character recognition system.

7. A supplemental device comprising:
an electromechanical switch arrangement having an open state and a closed state, wherein in the open state two electrical contacts of the electromechanical switch arrangement are electrically isolated from each other, and in the closed state the electromechanical switch arrangement provides a conductive path between the two electrical contacts, the electromechanical switch arrangement comprising:
a main body; and
a first protrusion configured to protrude from the main body such that the protrusion contacts a first surface of an injection device when any number of dose units are dialed into the injection device, wherein the open state or the closed state of the switch arrangement is configured to change, during dose dialing, when a dose dialed into the injection device moves the electromechanical switch arrangement from a one unit dose position to a zero unit dose position; and
a switching member having an open state and a closed state, the switching member comprising a second protrusion configured to contact a flange of the injection device only in the zero unit dose position of the electromechanical switch arrangement.

8. The supplemental device according to claim 7, further comprising a processor arrangement, wherein the processor arrangement is configured to determine whether the electromechanical switch arrangement and the switching member are open or closed.

9. The supplemental device according to claim 7, further comprising a processor arrangement, wherein the processor arrangement is configured to determine an amount of rotation of the first surface of the injection device from signals received from the electromechanical switch arrangement.

10. A system comprising a supplemental device comprising:
an electromechanical switch arrangement having an open state and a closed state, wherein in the open state two electrical contacts of the electromechanical switch arrangement are electrically isolated from each other, and in the closed state the electromechanical switch arrangement provides a conductive path between the two electrical contacts, the electromechanical switch arrangement comprising:
a main body; and
a protrusion configured to protrude from the main body such that the protrusion contacts a surface of an attached injection device in a zero unit dose position of the electromechanical switch arrangement, wherein the open state or the closed state of the switch arrangement is configured to change, during dose dialing, when a dose dialed into the attached injection device is moves the electromechanical switch arrangement from a one unit dose position to the zero unit dose position; a processor arrangement configured to:
detect one or more changes in the open state or the closed state of the electromechanical switch arrangement;
determine from the one or more changes in the open state or the closed state that the dose dialed into the injection device, during dose dialing, has moved from the one unit dose position to zero unit dose position; and
in response to determining from the one or more changes in the open state or the closed state that the dose dialed into the injection device moves the electromechanical switch arrangement from the one unit dose position to the zero unit dose position, change a display output of the supplemental device from a dose delivery display to a dispense-end display, and
the attached injection device.

11. The system according to claim 10, wherein the attached injection device comprises:
a housing;
a corrugated dialing sleeve rotatably supported within the housing, the corrugated dialing sleeve having a plurality of axially aligned corrugations; and
a rotatable dosage knob coupled to the corrugated dialing sleeve at a first end of the corrugated dialing sleeve, wherein the protrusion of the electromechanical switch arrangement is configured to engage the corrugated dialing sleeve.

12. The system according to claim 11, wherein each of a plurality of troughs forming the corrugations terminates at the first end of the corrugated dialing sleeve with a common incline or respective inclines.

13. The system according to claim 11, wherein the rotatable dosage knob has a larger diameter than a diameter of the corrugated dialing sleeve and defines a flange at the first end of the corrugated dialing sleeve.

* * * * *

UNITED STATES PATENT AND TRADEMARK OFFICE
CERTIFICATE OF CORRECTION

PATENT NO. : 10,744,269 B2
APPLICATION NO. : 14/888724
DATED : August 18, 2020
INVENTOR(S) : Robert Frederick Veasey et al.

Page 1 of 1

It is certified that error appears in the above-identified patent and that said Letters Patent is hereby corrected as shown below:

In the Claims

In Column 28, Line 25 (approx.), Claim 10, after "device" delete "is"

Signed and Sealed this
Twenty-seventh Day of October, 2020

Andrei Iancu
*Director of the United States Patent and Trademark Office*